United States Patent [19]

Yamano et al.

[11] Patent Number: 5,247,095
[45] Date of Patent: Sep. 21, 1993

[54] INTERMEDIATES FOR D-BIOTIN SYNTHESIS AND THEIR PRODUCTION

[75] Inventors: Toru Yamano, Itami; Kazuo Nakahama, Nagaokakyo; Kunio Takanohashi, Kawanishi, all of Japan

[73] Assignee: Takeda Chemical Industries, Ltd., Osaka, Japan

[21] Appl. No.: 935,105

[22] Filed: Aug. 27, 1992

[30] Foreign Application Priority Data

Aug. 27, 1991 [JP] Japan .................................. 3-215426
Dec. 24, 1991 [JP] Japan .................................. 3-341103

[51] Int. Cl.$^5$ ............................................. C07D 495/04
[52] U.S. Cl. ................................................... 548/303.7
[58] Field of Search .................................... 548/303.7

[56] References Cited

FOREIGN PATENT DOCUMENTS

| 503682 | 6/1954 | Canada . |
| 45-37775 | 11/1970 | Japan . |
| 45-87776 | 11/1970 | Japan . |
| 117486 | 11/1974 | Japan . |
| 57-198098 | 12/1982 | Japan . |

OTHER PUBLICATIONS

Tetrahedron, vol. 46, No. 23, 1990 (printed in Great Britain), pp. 7677-7676.

*Primary Examiner*—Joseph Paul Brust
*Assistant Examiner*—Mary Susan H. Gabilan
*Attorney, Agent, or Firm*—Wegner, Cantor, Mueller & Player

[57] ABSTRACT

There are disclosed a compound of the general formula (I):

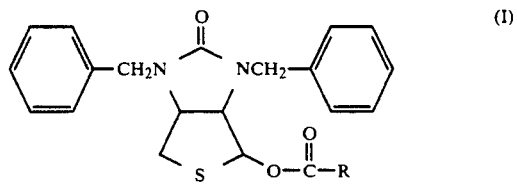

wherein the group R—CO— is an acyl group and its production. There is also disclosed a process for producing optically active ($\pm$)-(3a$\alpha$, 4$\alpha$, 6a$\alpha$)-tetrahydro-4-acetoxy-1,3-dibenzyl-1H-thieno[3,4-d]imidazol-2(3H)-one by using the compound (I). The compound (I) can be used as an intermediate for producing D-biotin which is useful as medicaments and feed additives for animals.

6 Claims, 4 Drawing Sheets

INTERMEDIATES FOR D-BIOTIN SYNTHESIS AND THEIR PRODUCTION

FIELD OF THE INVENTION

The present invention relates to novel intermediates for D-biotin synthesis and their production.

D-Biotin is also referred to as vitamin H and is a water-soluble vitamin necessary for higher animals and a lot of microorganisms. D-Biotin is a known compound represented by the formula:

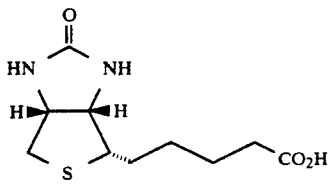

BACKGROUND OF THE INVENTION

As synthetic processes of D-biotin, for example, the process using a sugar as a starting material [Tetrahedron Letters, 2765 (1975)] and a process using L-cysteine as a starting material [J. Am. Chem. Soc., 97, 5936 (1975)] have been known. In these processes, optically active compounds are used as the starting materials and optically active D-biotin is obtained by stereoselective reactions.

Further, as other processes for producing D-biotin, there are, for example, a process wherein D-biotin is prepared by using an optically active lactone obtained by selective reduction of only a carboxyl group of a half ester according to the following reaction scheme (JP-A 59-84888):

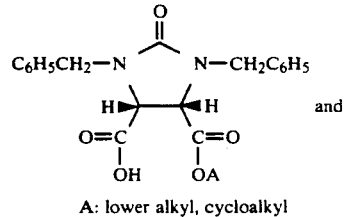

A: lower alkyl, cycloalkyl and a process wherein D-biotin is prepared by using an optically active lactone obtained from an optically active amidecarboxylic acid by esterification, reduction and hydrolysis according to the following reaction scheme (JP-B 60-3387):

C₆H₅CH₂N [structure] NCH₂C₆H₅ →esterification→ reduction→ hydrolysis→

A': lower alkyl, aralkyl
A": aralkyl having asymmetric carbon optically active lactone ----→ D - biotin
as described above JP-A 57-198098 discloses the production of an optically active monoester mono carboxylic acid by hydrolyzing the corresponding diester asymmetrically using an esterase. The optically active monoester-mono-carboxylic acid can be converted into cis-1,3-dibenzylhexahydro 1H-furo(3,4d)-imidazole 2,4-dione which is used as an intermediate for D-biotin synthesis by lactonization with lithium borohydride.

Furthermore, Tetrahedron, 46, 7667 (1990) discloses a process for producing D-biotin according to the following reaction scheme:

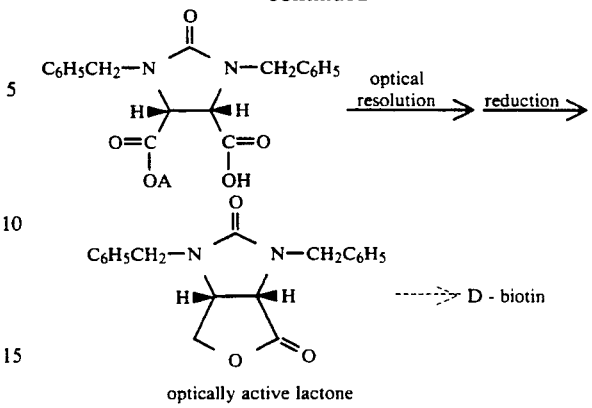

the above optically active lactone ----→ D - biotin and a process for producing the above halide by reduction of a compound of the formula:

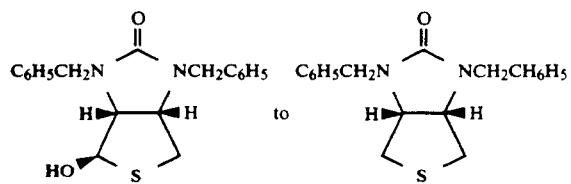

with triethylsilane, boron trifluoride followed by halogenation.

However, these processes are not suitable for the industrial production of D-biotin because each of them includes many reaction steps, reaction operations are complicated, and further the total yield is low.

Under these circumstances, the present inventors have studied D-biotin synthesis and investigated industrially advantageous processes for the production of optical active intermediates, intensively. As a result, it has been found that kinetic optical resolution using an enzyme as a catalyst is very advantageous to the production of intermediates for D-biotin synthesis. The present inventors have further continued the investigation based on this finding and have found a novel intermediate for D-biotin synthesis which is very useful for the kinetic optical resolution. When the novel intermediate is subjected to the kinetic optical resolution and then to a series of reactions, D-biotin having high optical purity can be obtained in high yield. Further, when this novel intermediate for D-biotin synthesis is used and an enzyme is suitably selected, the kinetic optical resolution can be efficiently employed in both hydrolysis of the novel intermediate and the production of the novel intermediate by acylation.

In this respect, recently, acylation catalyzed by an enzyme such as lipase or the like in an organic solvent have been reported one after another [J. Am. Chem. Soc., 113, 3166 (1991); Tetrahedron Letters, 33, 3231 (1992); etc.]. However, there are not so many enzymes which can exhibit their activities in an organic solvent and their use is restricted. Nevertheless, the above acylation can be efficiently carried out.

By the way, a biggest defect of optical resolution is that only one half of a starting material is utilized. The present inventors have also studied to overcome this problem. As a result, it has been found that the enantiomeric intermediate synthesis removed by the optical resolution can be used again as a starting material for the production of the novel intermediate for D-biotin synthesis by subjecting the enantiomeric intermediate to deacyloxylation. As a similar method, the above reduction of the hydroxy group with triethylsilane and boron trifluoride [Tetrahedron, 46, 7667 (1990)] has been reported. However, these reagents are expensive and can not be readily available. Further, they have high reactivity, which makes their handling very difficult. Furthermore, the reaction should be carried our under anhydrous conditions at a lower temperature. Therefore, it is not suitable for the industrial production.

Further, it has been found a certain known intermediate for D-biotin synthesis can be efficiently converted into another known intermediate useful for D-biotin synthesis by specific oxidation. As similar oxidation, Swern oxidation using dimethylsulfoxide (DMSO) and trifluoroacetic anhydride has been known [Tetrahedron, 46, 7667 (1990)]. However, since trifluoroacetic anhydride is expensive and the reaction should be carried out at a low temperature such as −60° C., it is not suitable for the industrial production. On the other hand, as a cheaper oxidizing agent with easy handling properties, a combination of DMSO and an activating agent has been known. Oxidation using such an oxidizing agent is known as Albright-Goldman oxidation and is advantageous because it can be carried out at room temperature. However, this oxidation is effective for only alcohols having large steric hindrance and, in the case of other compounds, the formation of by-products such as methylthiomethyl ether isomers and the like have been reported [J. Am. Chem. Soc., 87, 4214 (1965); Jikken Kagaku Koza, 4th ed., Vol. 23, p 318]. When this oxidation was applied to 4-hydroxyl group of the compound (II') as described hereinafter, acetylation predominantly proceeded and only a little objective compound was obtained. Nevertheless, when this oxidation is applied to the production of the above intermediate for D-biotin production under conditions different from ordinary employed conditions, surprisingly, the intermediate can be obtained with minimizing the formation of by-products and the desired oxidation product can be obtained in high yield.

OBJECTS OF THE INVENTION

One object of the present invention is to provide novel compounds useful as intermediates for D-biotin synthesis.

Another object of the present invention is to provide industrially advantageous processes for producing such intermediates.

Still another object of the present invention is to provide industrially advantageous processes for producing known intermediates for D-biotin synthesis.

These objects as well as other objects and advantages of the present invention will become apparent to those skilled in the art from the following description with reference to the accompanying drawings.

Figure 1:
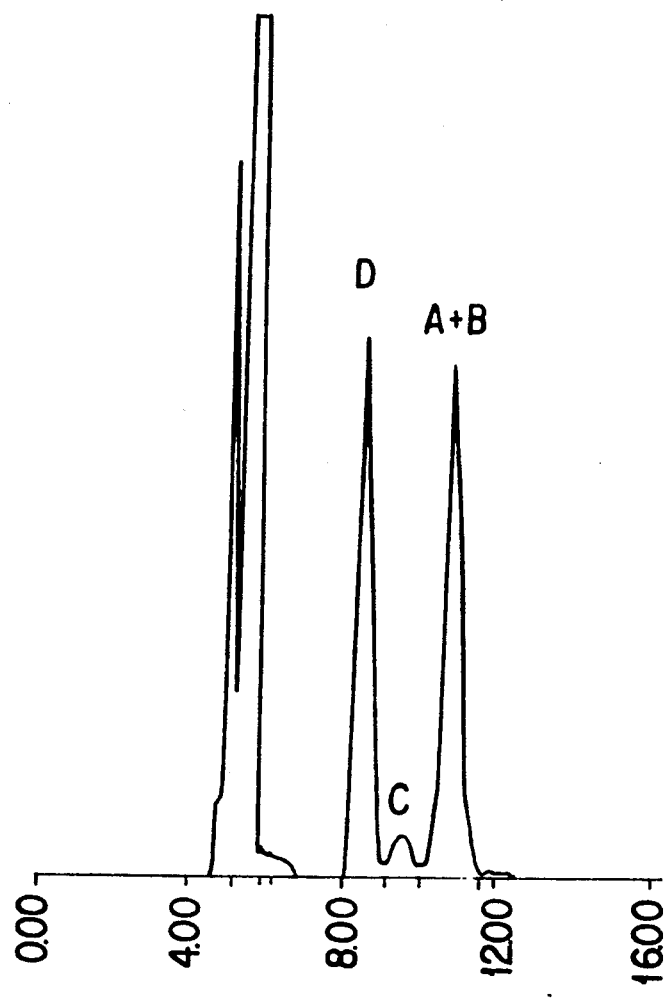
FIG. 1 shows a chromatogram obtained by high performance liquid chromatography of the reaction mixture obtained in Example 10 hereinafter.

The abscissa of FIG. 1 indicates the retention time (minutes).

Figure 2:
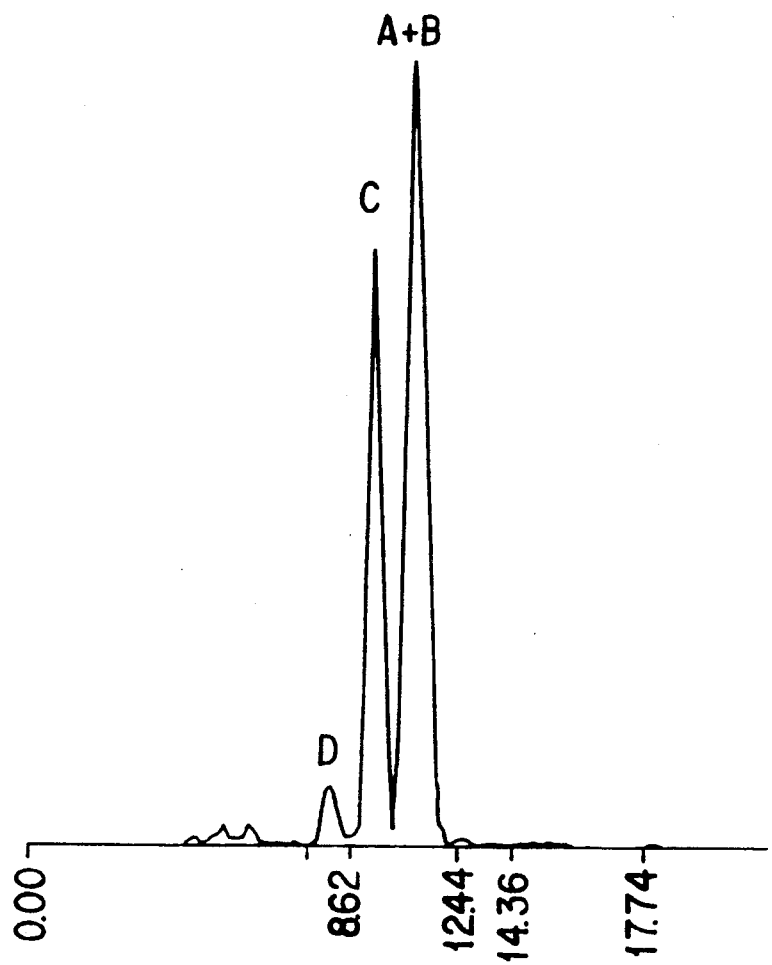

FIG. 2 shows a chromatogram obtained by high performance liquid chromatography of the reaction mixture obtained in Example 11 hereinafter.

The abscissa of FIG. 2 indicates the retention time (minutes).

Figure 3:
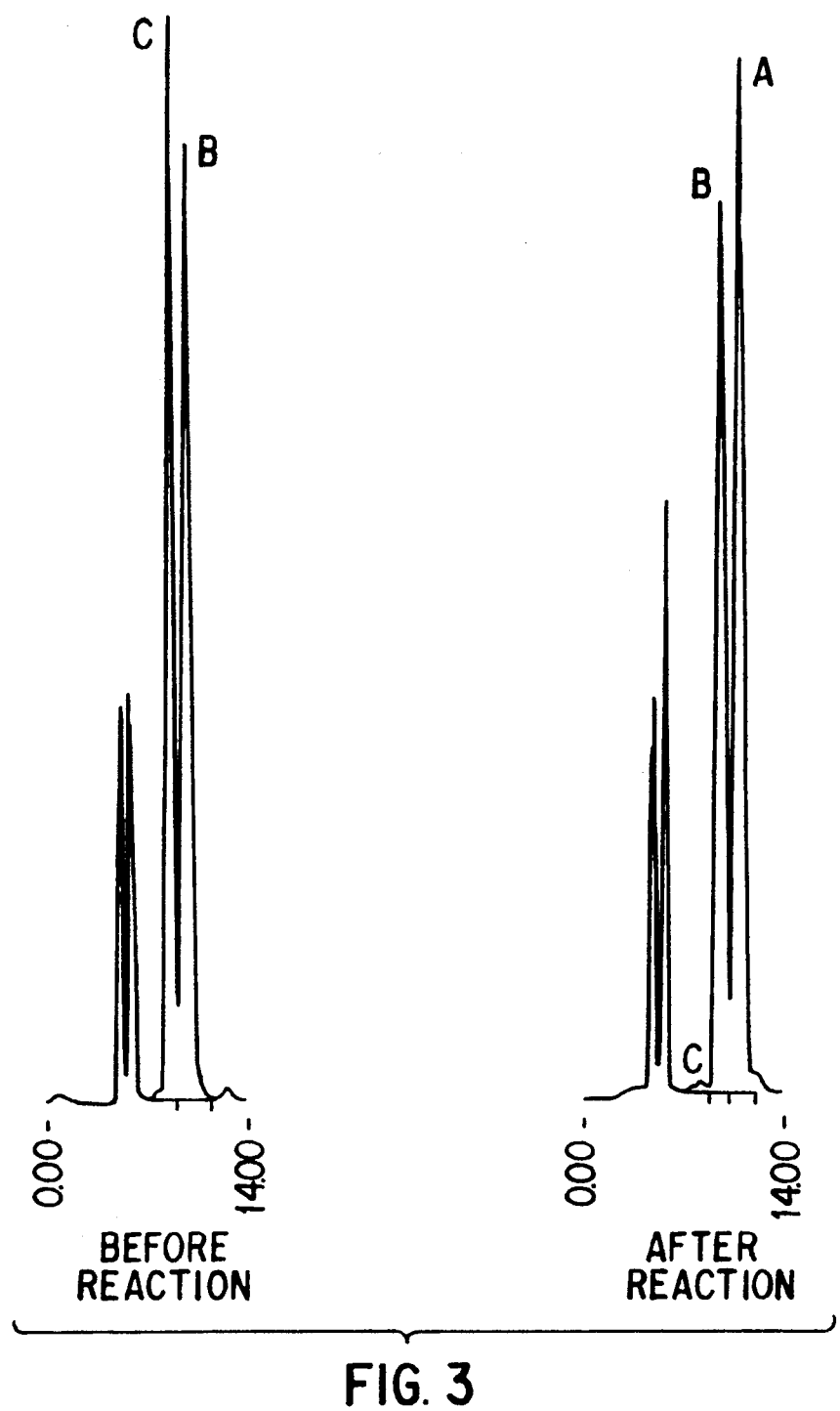

FIG. 3 shows a high performance liquid chromatogram obtained in Example 28 hereinafter.

Figure 4:
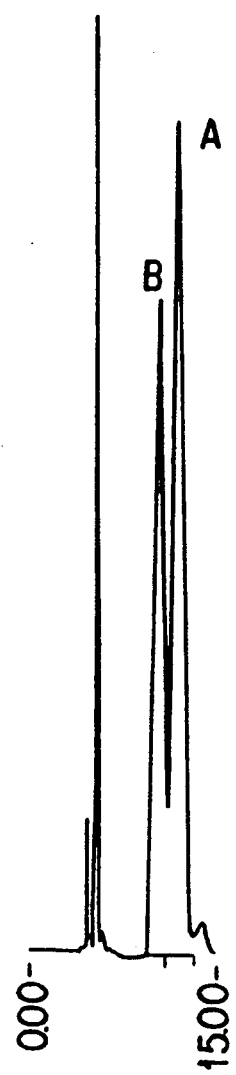

FIG. 4 shows a high performance liquid chromatogram obtained in Example 29 hereinafter.

In the drawings, A represents a peak of a compound of the formula (Ia'):

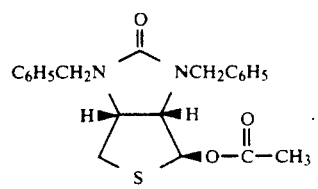

B represents a peak of a compound of the formula (Ib'):

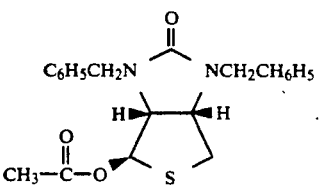

C represents a peak of the compound of the formula (IIa):

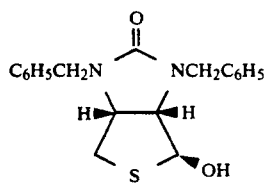

D represents a peak of the compound of the formula (IIb):

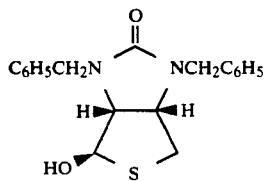

SUMMARY OF THE INVENTION

According to the present invention, there are provided:

(1) A compound of the formula (I):

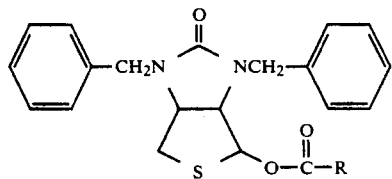

wherein

is an acyl group, inclusive its racemic modification and its 4-α optically active isomer of a compound of the formula (I') or (I''):

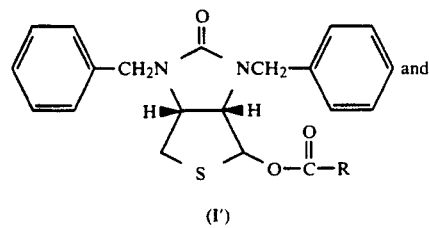

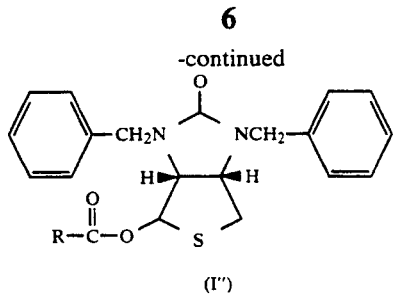

(2) A process for producing an optically active compound of the formula (II') or (II''):

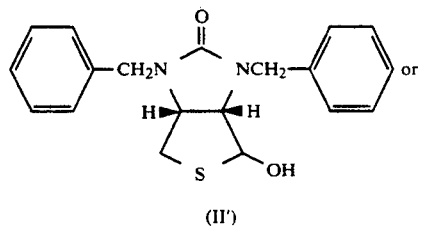

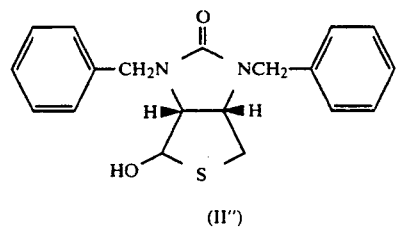

which comprises contacting a mixture of the compounds of the formula (I') and (I'') with a culture of a microorganism selected from microorganisms belonging to the genera Acetobacter, Bacillus, Brevibacterium, Pseudomonas, Streptomyces, Ampullariella, Candida and Trichosporon being capable of deacylating either one of the acyl groups more readily than the other, or its processed matter;

(3) A process for producing the compound of the formula (I) which comprises acylating a compound of the formula (II):

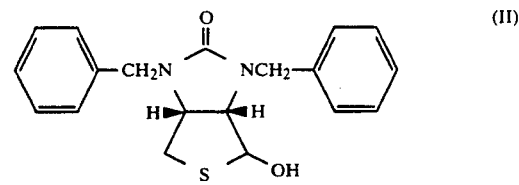

inclusive its racemic modification and the optically active compounds of the formulas (II') and (II'');

(4) A process for producing the compound of the formula (I) which comprises reacting a compound of the formula (III):

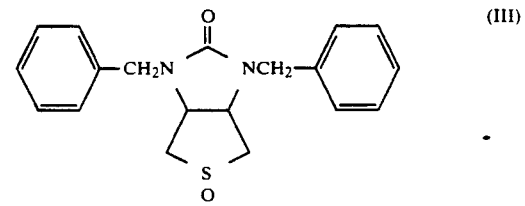

with an organic carboxylic acid anhydride:

(5) A process for producing a compound of the formula (VI):

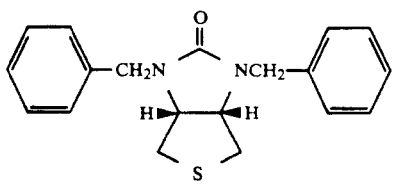

which comprises subjecting the compound of the formula (I″) to deacyloxy reaction;

(6) A process for producing the compound (I′) or (I″) which comprises contacting a mixture of the compounds (II′) and (II″) with a esterase derived from bacteria and being capable of acylating either one of the hydroxy groups more readily than the other in the presence of an acyl group donor;

(7) A process for producing a compound of the formula (VII):

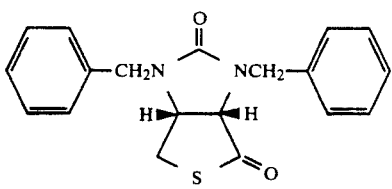

which comprises oxidizing the compound of the formula (II′) with dimethylsulfoxide and an activating agent; and (8) A process for producing a compound of the formula (VII) which comprises contacting a mixture of the compounds (II′) and (II″) with an esterase derived from bacteria and being capable of acylating either one of the hydroxy groups more readily than the other in the presence of an acyl group donor, removing the compound (I′) or (I″) formed to obtain the compound (II′) and oxidizing the compound (II′).

DETAILED DESCRIPTION OF THE INVENTION

Examples of the acyl group of the formula: R—CO— in the formulas (I), (I′) and (I″) include acyl groups derived from organic carboxylic acids such as formyl, alkylcarbonyl (alkanoyl), preferably $C_{1-6}$ alkyl-carbonyl (e.g., acetyl, propionyl, butyryl, isobutyryl, valeryl, isovaleryl, pivaloyl, hexanoyl, etc.), arylcarbonyl (aroyl), preferably $C_{6-14}$ aryl-carbonyl (e.g., benzoyl, 1- or 2-naphthoyl, etc.), aralkylcarbonyl, preferably $C_{7-19}$ aralkyl-carbonyl (e.g., benzylcarbonyl, 2-phenethylcarbonyl, 1 or 2-naphthylmethylcarbonyl, benzhydrylcarbonyl, etc.) and the like. These groups may be substituted with nitro, halogen (e.g., fluorine, chlorine, bromine etc.), hydroxyl, oxo, carbamoyl, $C_{1-4}$ alkyl (e.g., methyl, ethyl, propyl, isopropyl, butyl, etc.), $C_{1-4}$ alkoxy (e.g., methoxy, ethoxy, propoxy, butoxy, etc.), optionally esterified carboxyl, $C_{1-4}$ alkoxyimino optionally substituted with carboxyl (e.g., methoxyimino, ethoxyimino, carboxymethoxyimino, 1-carboxy-1-methylethoxyimino, etc.) and the like.

The group of the formula: R—CO— is preferably formyl, $C_{1-6}$ alkyl-carbonyl optionally substituted with carboxyl group (e.g., acetyl, propionyl, butyryl, isobutyryl, valeryl, isovaleryl, pivaloyl, hexanoyl, carboxyacetyl, 3-carboxypropionyl, etc.), more preferably $C_{1-6}$ alkyl carbonyl (e.g., acetyl, propionyl, butyryl, isobutyryl, valeryl, isovaleryl, pivaloyl, hexanoyl, etc.).

The compound (I) has three asymmetric carbons and the following 8 optical isomers of (Ia) to (Ih) exist.

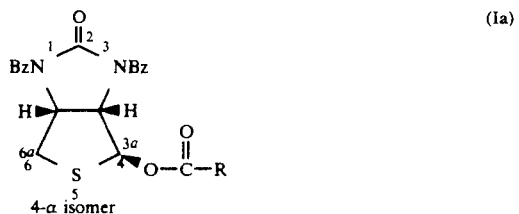

(Ia)

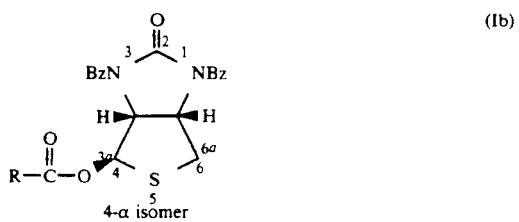

(Ib)

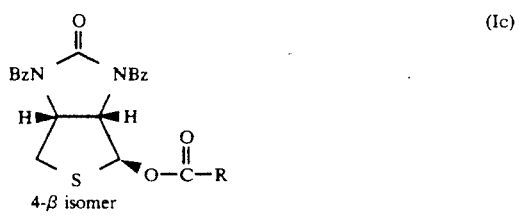

(Ic)

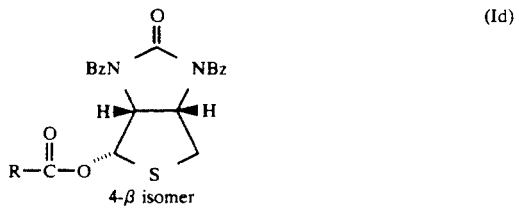

(Id)

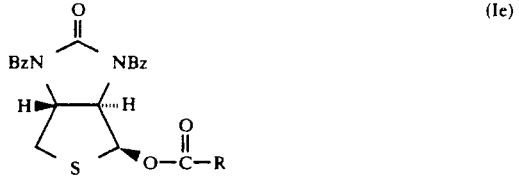

(Ie)

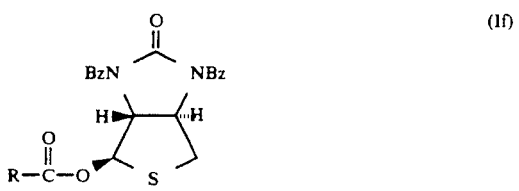

(If)

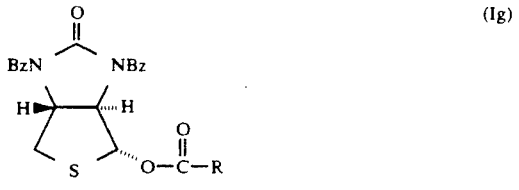

(Ig)

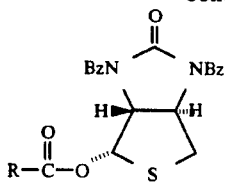

(Ih)

wherein Bz is benzyl group and the position numbers are indicated on the atoms constituting the ring.

When the compound (I), (I') or (I'') has a carboxyl group in the molecule, the compound may form its salt.

As the salt of the compound (I), there are, for example, salts with inorganic bases and salts with organic bases. Examples of the inorganic base include alkaline metals (e.g., sodium, potassium, etc.), alkaline earth metals (e.g., calcium, magnesium, etc.) and the like. Examples of the organic base include trimethylamine, triethylamine, pyridine, picoline, N,N-dibenzylethylenediamine, ethanolamine, diethanolamine, trishydroxymethylaminomethane, dicyclohexylamine, morphine, cinchonidine, cinchonine, quinine and the like.

The compound (I) can be prepared according to per se known processes, for example, the process described in J. Chem. Edu., 57, 220 (1980) or the process described in Berichte, 43, 1401 (1910).

Further, the compound (I) can be prepared according to the processes of the following Preparation 1 or 2.

Preparation 1

The compound (I) can be prepared by acylating the compound (II). As the acylating agent to be used in the present reaction, there are carboxylic acid (IV) of the formula:

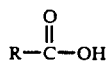

(IV)

wherein R is as defined above or its reactive derivative. As the reactive derivative, there can be used, for example, acid halides, acid anhydrides, active amides, active esters, active thioesters and the like which can be prepared according to conventional methods. Specifically, the following reactive derivatives can be used.

(1) Acid Halides

There can be used, for example, acid chloride, acid bromide and the like.

(2) Acid Anhydrides

There can be used, for example, symmetric acid anhydrides, namely, (RCO)$_2$, mono C$_{1-6}$ alkyl carbonate mixed anhydride and the like.

(3) Active Amides

There can be used, for example, amides formed with pyrazole, imidazole, 4-substituted imidazole, dimethylpyrazole, benzotriazole and the like.

(4) Active Esters

There can be used, for example, esters such as methoxymethyl ester, benzotriazole ester, 4-nitrophenyl ester, 2,4-dinitrophenyl ester, trichlorophenyl ester, pentachlorophenyl ester or the like, esters formed by 1-hydroxy-1H-2-pyridone, N-hydroxysuccinimide, N-hydroxyphthalimide or the like.

(5) Active Thioesters

There can be used, for example, thio esters formed by heterocyclic thiols such as 2-pyridylthiol, 2-benzothiazolylthiol and the like.

As the method of the acylation, there can be used, for example, the method in which the starting material (II) is acylated with the carboxylic acid (IV) in the presence of a carbodiimide. Any carbodiimide can be used in so far as it has a carbodiimide bond (—N=C=N—) which can be converted to a urea bond (—NH—CO—NH—) in this acylating reaction. Example thereof include the compound of the formula (V):

$$R_1-N=C=N-R_2 \qquad (V)$$

wherein R$_1$ and R$_2$ each are organic residues which can convert the carbodiimide bond into the urea bond.

The organic residues represented by R$_1$ and R$_2$ can be appropriately selected from, for example, di-C$_{1-6}$ alkyl, C$_{3-7}$ cycloalkyl optionally having an amino group, C$_{1-6}$ alkyl optionally having di-C$_{1-6}$ alkylamino or morpholino group, or phenyl optionally having a C$_{1-6}$ alkyl group and the like. As the carbodiimides, dicyclohexylcarbodiimide is practically preferred. Other examples thereof include diphenylcarbodiimide, di-o-tolylcarbodiimide, di-p-tolylcarbodiimide, di-tert-butylcarbodiimide, 1-cyclohexyl-3-(2-morpholinoethyl)carbodiimide, 1-cyclohexyl-3-(4-diethylaminocyclohexyl)-carbodiimide, 1-ethyl-3-(2-diethylaminopropyl)carbodiimide and 1-ethyl-3-(3-dimethylaminopropyl)carbodiimide and the like.

The amount of the carboxylic acid (IV) to be used may be about 1 mole or more, preferably about 1 to 30 moles based on the starting material (II).

The amount of the carbodiimide (V) to be used may be, for example, about 1 to 700 moles, preferably about 1 to 50 moles, more preferably about 1 to 5 moles based on the starting material (II).

The reaction is carried out in a solvent which dose not hinder the reaction or in the absence of a solvent. Examples of the solvent which dose not hinder the reaction include ketones (e.g., acetone, etc.), ethers (e.g., diethyl ether, tetrahydrofuran, dioxane, etc.), nitriles (e.g., acetonitrile, etc.), hydrocarbons (e.g., benzene, toluene, xylene, etc.), halogenated hydrocarbons (e.g., dichloromethane, chloroform, 1,2-dichloroethane, etc.), esters (e.g., ethyl acetate, etc.), amides (e.g., dimethylformamide, dimethylacetamide, etc.), tert-amines (e.g., triethylamine, tributylamine, N-methylmorpholine, N-methylpiperidine, N,N-dimethylaniline, etc.), pyridines (e.g., pyridine, picoline, lutidine, collidine, etc.) and the like.

The solvents can be used alone or in combination thereof in an appropriate mixing ratio.

The acylation proceeds more advantageously by using a catalyst which can promote the acylation of the starting material (II). As the catalyst, there can be used, for example, base catalysts and acid catalysts. As the base catalyst, there can be used, for example, tert-amines such as aliphatic tert-amines (e.g., triethylamine, etc.) and aromatic tert-amines (e.g., pyridine, α-, β- or γ-picoline, 2,6-lutidine, 4-dimethylaminopyridine, 4-(1-pyrrolidinyl)pyridine, dimethylaniline, diethylaniline, etc.); halogenated alkaline metals (e.g., potassium fluoride, anhydrous lithium iodide, etc.); organic acid salts (e.g., sodium acetate, etc.) and the like. As the acid catalyst, there can be used, for example, lewis acids [e.g., anhydrous zinc chloride, anhydrous aluminium chloride (AlCl$_3$), titanium tetrachloride (TiCl$_4$), tin tetrachloride (SnCl$_4$), antimony pentachloride, cobalt chloride, cupric chloride, boron trifluoride etherate, etc.], inorganic strong acids (e.g., sulfuric acid, perchloric acid, hydrogen chloride, hydrogen bromide, etc.), organic strong acids (e.g., benzenesulfonic acid, p toluenesulfonic acid, trifluoroacetic acid, trichloroacetic acid, etc.), acidic ion-exchange resins (e.g., polystyrene sulfonic acid, etc.) or the like. Among the above catalysts, pyridine, 4-dimethylaminopyridine, sulfuric acid and the like are preferred.

The amount of the catalyst to be used may be catalytic amount that can promote the acylation of the starting material (II) with the carboxylic acid (IV), normally about 0.001 to 10 moles, preferably about 0.001 to 1 moles based on the compound (IV). In many cases, use of the catalyst greatly improves the yield of the compound (I). Further, the carboxylic acid (IV) to be used can be saved. For example, the amount of the carboxylic acid (IV) may often be about 1 to 10 moles based on the starting material (II).

The reaction temperature is not specifically limited, and is normally about $-30°$ to $100°$ C., preferably about $10°$ to $50°$ C. The reaction time is several minutes to several tens hours, for example, about 5 minutes to 30 hours.

As the solvent, catalyst and molar ratio in the acylation using the reactive derivative of the carboxylic acid (II), there can be used the same solvent, catalyst and molar ratio as those in the above acylation in the presence of the carbodiimides (V). The reaction temperature is normally about $-40°$ to $100°$ C., preferably about $-20°$ to $40°$ C. The reaction mixture may be warmed to higher temperature to speed up the reaction.

The reaction time is about several minutes to several tens hours.

Preparation 2

The compound (I) can be prepared by reacting the compound (III) with an organic carboxylic acid anhydride.

As the organic carboxylic acid anhydride to be used in the reaction, there are, for example, $C_{1-6}$ alkylcarboxylic acid anhydride (e.g., acetic anhydride, propionic anhydride, butanoic anhydride, etc.) and the like.

The reaction can be carried out in a solvent which does not hinder the reaction or in the absence of a solvent.

Examples of the solvent which dose not hinder the reaction include ketones (e.g., acetone, etc.), ethers (e.g., diethyl ether, tetrahydrofuran, dioxane, etc.), nitriles (e.g., acetonitrile, etc.), hydrocarbons (e.g., benzene, toluene, xylene, etc.), halogenated hydrocarbons (e.g., dichloromethane, chloroform, 1,2-dichloroethane, etc.), esters (e.g., ethyl acetate, etc.), amides (e.g., dimethylformamide, dimethylacetamide, etc.) and the like. The solvents can be used alone or in combination thereof in an appropriate mixing ratio.

The amount of the organic carboxylic acid anhydride to be used may be, for example, about 1 mole or more based on the starting material (III), and is preferably about 1 to 30 moles, more preferably about 1 to 2 moles based on the starting material (III).

This reaction proceeds more advantageously by using a catalyst being capable of promoting the reaction. As the catalyst, there can be used, for example, acid catalysts.

As the acid catalyst, there can be used, for example, lewis acids [e.g., anhydrous zinc chloride, anhydrous aluminium chloride (AlCl$_3$), titanium tetrachloride (TiCl$_4$), tin tetrachloride (SnCl$_4$), antimony pentachloride, cobalt chloride, cupric chloride, boron trifluoride etherate, etc.], inorganic strong acids (e.g., sulfuric acid, phosphoric acid, perchloric acid, hydrogen chloride, hydrogen bromide, etc.), organic strong acids (e.g., benzenesulfonic acid, p-toluenesulfonic acid, trifluoroacetic acid, trifluoromethanesulfonic acid, trichloroacetic acid, etc.), acidic ion-exchange resins (e.g., polystyrene sulfonic acid, etc.) and the like.

The amount of the catalyst to be used is normally about 0.01 to 10 moles, preferably about 0.01 to 2 moles based on the compound (III).

The reaction temperature is about $-20°$ to $100°$ C., preferably about $10°$ to $60°$ C.

The reaction time is several minutes to several tens hours.

The reaction product obtained by the method of the above Preparations 1 or 2 can be isolated and purified according to known manners such as solvent extraction, change of nature of solution, conversion of solvent, salting out, crystallization, recrystallization, chromatography and the like.

The compound (II') or (II") can be prepared by contacting the mixture of the compounds (I') and (I") with a culture of a microorganism belonging to the genera Acetobacter, Bacillus, Brevibacterium, Pseudomonas, Streptomyces, Ampullariella, Candida or Trichosporon being capable of deacylating either one of the acyl groups more readily than the other, or its processed material.

The microorganism to be used in the process of the present invention may be any microorganism being capable of deacylating either one of the compounds (I') and (I") more readily than the other. Examples thereof include bacteria, fungi and the like.

As the bacteria, there can be used, for example, those belonging to genera Acetobacter, Bacillus, Brevibacterium, Pseudomonas, Streptomyces, Ampullariella and the like. Preferred examples of the Acetobacter include *Acetobacter rancens* IFO 3298 and the like. Preferred examples of the Bacillus include *Bacillus cereus* IFO 3003, *Bacillus megaterium* IFO 13498, *Bacillus megaterium* IFO 12108 and the like. Preferred examples of the Brevibacterium include *Brevibacterium iodinum* IFO 3558 and the like. Preferred examples of the Pseudomonas include *Pseudomonas aeruginosa* IFO 3445, *Pseudomonas aeruginosa* IFO 3447, *Pseudomonas aeruginosa* IFO 3448 and the like. Examples of the Streptomyces to be used include *Streptomyces rochei var. volubilis* IFO 12507 and the like. Examples of the Ampullariella to be used include *Ampullariella digitata* IFO 12512 and the like.

As the fungi, there can be used, for example, those belonging to the genera Candida, Trichosporon and the like. Preferred examples of the Candida include *Candida guilliermondii* ATCC 14242 and the like. Preferred examples of the Trichosporon include *Trichosporon fermentans* IFO 1199 and the like.

The above strains having the IFO accession numbers are available from Institute of Fermentation, Osaka, Japan. The strain having the ATCC accession number is available from American Type Culture Collection, Maryland, U.S.A.

The above microorganisms may be used as they are. Or, mutants thereof having improved deacylating activities or specificity may also be used.

This process of the present invention is carried out by contacting the starting material with a culture of the above microorganism or its processed matter. The microorganism is cultivated in a medium containing, as carbon sources, glucose, sucrose, dextrin, soluble starch and the like, and, as nitrogen sources, organic or inorganic nitrogen-containing materials (e.g., meat extract, peptone, yeast extract, corn steep liquor, amino acids, ammonium sulfate, ammonium nitrate, ammonium chloride, etc.), inorganic materials (e.g., magnesium chloride, sodium chloride, etc.) and the like. The cultivation is carried out under still, aeration or shaking conditions. The temperature is about 20° to 45° C., preferably about 28° to 37° C. The pH is about 6 to 9, preferably about 6.8 to 7.8. The cultivation is carried out for about 10 to 96 hours, preferably for about 16 to 72 hours.

The "culture" used in the present invention is a culture solution obtained by the cultivation of the above microorganisms. The "processed matter" includes, for example, cells or culture supernatant obtained by filtration or centrifugation of the culture; disrupted cells or cell extracts obtained by sonication, French press, alumina grinding or treatment with a lytic enzyme, a surfactant, an organic solvent or the like; and purified deacylation enzymes obtained from culture supernatant or cell extracts by ammonium sulfate fractionation, ion exchange chromatography, adsorption chromatography, affinity chromatography or the like.

In this reaction, the concentration of the starting material in the reaction mixture is about 0.1 to 100 mg/ml, preferably about 1 to 10 mg/ml. The amount of the culture or its processed matter to be added is suitably 1 to 50 mg by wet cell weight per 1 ml of the reaction mixture. The reaction temperature is about 15° to 80° C., preferably about 24° to 42° C. The pH is about 4 to 11, preferably about 6 to 9. The reaction time is about 10 minutes to 72 hours, preferably about 1 to 24 hours. A reaction activator in an organic solvent, enzyme stabilizer or the like may optionally be added to the reaction mixture. The reaction can be carried out under any of still, shaking or agitating conditions. Further, if necessary, the deacylation enzyme may be immobilized on a suitable carrier and reacted in a bioreactor.

In the present invention, the compound (I') or (I") can also be produced by selectively acylating a mixture of the compounds (II') and (II") with an esterase derived from bacteria and being capable of acylating either one of the hydroxy groups more readily than the other in the presence of an acyl group donor.

Examples of the bacteria which produce the esterase include those belonging to the genera Pseudomonas, Streptomyces, Bacillus, Acetobacter and the like. For example, there is Pseudomonas PS-21 (FERM-P 7026, JP-B 63-3594), *Bacillus megaterium* IFO 13498, *Pseudomonas aeruginosa* IFO 3447, *Pseudomonas aeruginosa* IFO 3448, *Acetobacter reancens* IFO 3298, *Streptomyces rochei var. volubilis* FERM P-6155 and the like. The above strains having the IFO accession numbers are available from Institute of Fermentation, Osaka, Japan.

The esterase can be prepared according to a conventional method. For preparing the esterase from a bacterium, the bacterium is cultivated according to a conventional method and the resulting culture is centrifuged to obtain a culture supernatant and cells. The cells are disrupted by sonication, French press, alumina grinding, treatment with lytic enzyme or the like, and centrifuged to obtain a cell extract. A purified esterase can be obtained from the above supernatant and cell extract by precipitation with a organic solvent, ammonium sulfate fractionation, ion exchange chromatography, adsorption chromatography, affinity chromatography or the like. The esterase to be used may be a culture or a crude material (e.g., the above culture supernatant, cell extract, etc.), a partially purified enzyme or a single pure enzyme. A culture solution itself as well as cells and supernatant can be used as the esterase.

Examples of the esterase include lipoprotein lipase (LPL) derived from Pseudomonas as described in JP-B 63-3594.

The above-described esterase can be used in the acylation reaction as it is or its can be immobilized on a suitable carrier. Examples of the carrier include polysaccharide derivatives such as cellulose, copolymerized amino acids, maleic anhydride derivatives, synthetic polymers such as styrene resin, activated carbon, and inorganic compounds such as porous glass, diatomaceous earth, alumina, silica gel and the like.

The acyl group donor is not specifically limited and it may be any donor being capable of specifically acylating either one of the compounds (II') and (II").

Examples of the acyl group include those described with respect to the group R—CO— in the formulas (I), (I') and (I") and there can be any of the above-described acylating agents as the acyl group donor. When the acyl group is acetyl, there can be used, for example, acetic anhydride, ethyl acetate, vinyl acetate, phenyl acetate or 2,2,2-trifluoroethyl acetate as the acyl group donor.

When a culture solution or cells are used as the esterase, the acyl group donor may not be necessarily used.

Although this acylation reaction can proceed in water, it is preferred to carry our the reaction in an organic solvent. As the organic solvent, there can be used a solvent which does not hinder the reaction. Examples of the organic solvent include ketones (e.g., acetone, etc.), ethers (e.g., diethyl ether, tetrahydrofuran, etc.) nitriles (e.g., acetonitrile, etc.), hydrocarbons (e.g., benzene, toluene, etc.), esters (e.g., ethyl acetate, etc.), amides (e.g., dimethylformamide, etc.) and halogenated hydrocarbons (e.g., dichloromethane, chloroform, etc.). These solvents can be used alone or in combination thereof. The concentration of the compounds (II') and (II") in the reaction mixture is about 0.1 to 100 mg/ml, preferably about 1 to 10 mg/ml. The reaction temperature is about 15° to 80° C., preferably about 24° to 42° C. The reaction time is about 10 minutes to 72 hours, preferably about 1 to 24 hours. Optionally, an enzyme stabilizer, a dehydrating agent such as molecular sieves, or water substitute such as DMSO, formamide, ethylene glycol or the like. The reaction can be carried out on standing, with shaking or with stirring. When the esterase is immobilized on a carrier, a bioreactor can be used.

In the above description, the compound (I') is preferably the compound (Ia). The compound (I") is preferably the compound (Ib). The compound (II') is preferably the compound of the formula (IIa):

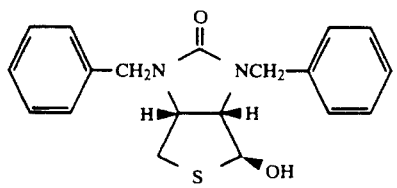

(IIa)

The compound (II'') is preferably the compound of the formula (IIb):

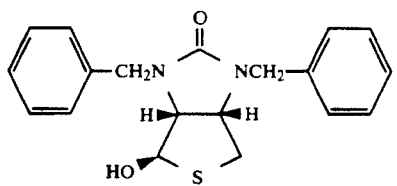

(IIb)

The reaction product can be isolated and purified by known manners such as solvent extraction, change of solution nature, conversion of solvent, salting out, crystallization, recrystallization, chromatography and the like.

To separate the desired optically active compound e.g., the compound (IIa), (IIb), etc.], per se known methods or modifications thereof can be used. As such a method, there can be used, for example, fractionation methods utilizing differences in solubility, crystallinity or the like, separation methods by chromatography, and the like.

For example, the compound (IIa) can be obtained by using the fractionation methods as follows.

The above mixture of the optical isomers is dissolved by heating in a specific solvent to prepare a supersaturated solution. Only the compound (IIa) can be fractionated and crystallized by cooling or concentrating the solution or by adding a solvent which decreases solubility of the compound (IIa). The fractionation and crystallization can be carried out in an inert solvent, and the compound (IIa) can be crystallized efficiently only when a specific solvent is used.

As the suitable solvent, there can be used, for example, ketones (e.g., acetone, etc.), alcohols (e.g., isopropyl alcohol, etc.), and mixed solvents of esters (e.g., ethyl acetate, etc.) and hydrocarbons (e.g., hexane, etc.). Especially preferred examples of the solvent include ketones such as acetone and the like. To obtain only the compound (IIa) by fractionation and crystallization, it is preferred that the content of the compound (IIa) is higher. When acetone is used as the solvent, the content of the compound (IIa) may be about 14% by weight based on the compound (Ib) in the above mixture. The temperature used in the present invention is preferably about −20° C. to the boiling point of the solvent used. However, the crystallization temperature of the compound (IIa) or lower is advantageous. The seed crystals of the compound (IIa) can be inoculated, but the inoculation is not always necessary because the compound (IIa) crystallizes spontaneously.

On the other hand, when the unreacted compound (I'') remains in the above mixture, the undesired compound (I'') can be subjected to deacyloxy reaction to convert it into the compound (VI).

The deacyloxy reaction of the present invention is shown in the following scheme:

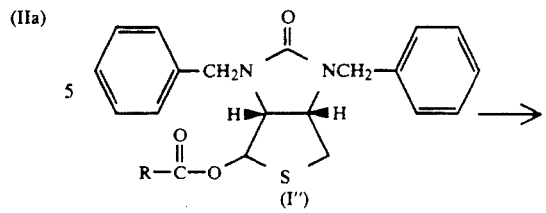

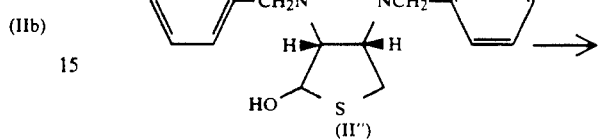

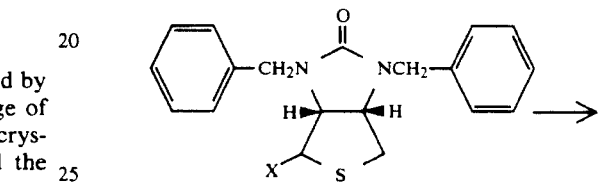

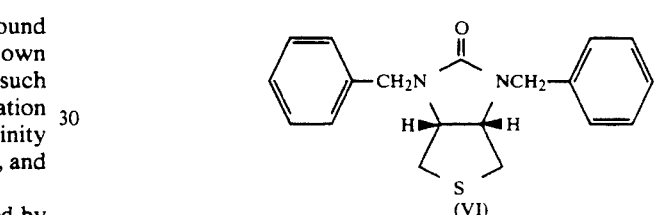

wherein

is an acyl group and X is a halogen. In the reaction, the compound (I'') is hydrolyzed to obtain the compound (II''), which is then led to the halide. The halide is reduced to obtain the compound (VI).

The hydrolysis of the compound (I'') to the compound (II'') shown in the above reaction scheme can be carried out by conventional basic hydrolysis. The hydrolysis can be carried out in any conventional organic solvent. Preferred examples of the solvent include lower alcohols (e.g., methanol, ethanol, etc.), ethers (e.g., diethyl ether, tetrahydrofuran, dioxane, etc.) and the like. As the base, any conventional base can be used. Preferred examples of the base include alkaline metal carbonates (e.g., sodium carbonate, sodium bicarbonate, potassium carbonate, etc.), alkaline metal hydroxides (e.g., sodium hydroxide, potassium hydroxide, lithium hydroxide, etc.), alkaline earth metal hydroxides (e.g., magnesium hydroxide, calcium hydroxide, etc.) and the like. The amount of the base to be used is about 1 to 10 moles, preferably about 1 to 3 moles. In the hydrolysis, the reaction temperature is not specifically limited, and is normally about 0° to 100° C., preferably about 15° to 40° C.

The reaction time is several minutes to several tens hours.

The halogenation of the compound (II'') can be carried out in any conventional halogenating agent. Examples of the halogenating agent include hydrogen halides (e.g., hydrogen chloride, hydrogen bromide, hydrogen iodide, etc.), phosphorus halides (e.g., phosphorus trichloride, phosphorus pentachloride, phosphorus tribromide, phosphorus pentabromide, phosphorus triiodide, etc.), thionyl halides (e.g., thionyl chloride, thionyl bromide, etc.), sulfuryl halides (e.g., sulfuryl chloride, etc.), active alkyl halides (e.g., triphenylphosphine-carbon tetrachloride, diphenyltrihalogenophosphorane, triphenylphosphine dihalogenide, phosphonic triphenyldihalogenide, etc.). The amount of the halogenating agent to be used is normally about 0.3 to 10 moles, preferably about 0.3 to 3 moles. Representative examples of the solvent to be used include ethers (e.g., diethyl ether, tetrahydrofuran, dioxane, etc.), nitriles (e.g., acetonitriles, etc.), hydrocarbons (benzene, toluene, etc.), esters (ethyl acetate, etc.), halogenated hydrocarbons (e.g., dichloromethane, chloroform, 1,2-dichloroethane, etc.) and the like. These solvents may be used alone or in combination thereof in appropriate ratios. The reaction temperature is not specifically limited, and is normally about −30° to 100° C., preferably −10° to 30° C. The reaction time is several minutes to several tens hours. The halide can be isolated, but may be used in the next step without purification.

The reduction of the halide can be carried out by catalytic hydrogenation or with hydride reducing agents. The catalytic hydrogenation can be carried out by any conventional methods. Examples of the catalyst include palladium-carbon, palladium-barium sulfate, platinum, Raney nickel and the like. Examples of the solvent to be used in the catalytic hydrogenation include conventional organic solvents such as lower alcohols (e.g., methanol, ethanol, etc.), ethers (e.g., diethyl ether, tetrahydrofuran, dioxane, etc.), nitriles (e.g., acetonitriles, etc.), hydrocarbons (benzene, toluene, etc.), esters (ethyl acetate, etc.), halogenated hydrocarbons (e.g., dichloromethane, chloroform, 1,2-dichloroethane, etc.), organic acids (e.g., ethyl acetate, etc) and the like. These solvents may be used alone or in combination thereof. The reaction temperature and pressure are not specifically limited, and are about 5° to 100° C. and atmospheric pressure to 100 atm, respectively.

The reaction time is several minutes to several tens hours.

The reduction with hydride reducing agents can be carried out by using borohydrides (e.g., sodium borohydride, magnesium borohydride, diborane, etc), aluminium hydrides (e.g., lithium aluminium hydride, diisobutylaluminium hydride, sodium diethyldihydroaluminate, etc.). It is preferred that the solvent is inert against the reducing agent under reaction conditions and can dissolve at least a part of the reagents. As the solvent, there can be used conventional organic solvents, for example, ethers (e.g., diethyl ether, tetrahydrofuran, dioxane, diethylene glycol dialkyl ether, etc.), hydrocarbons (benzene, toluene, etc.), halogenated hydrocarbons (e.g., dichloromethane, chloroform, 1,2-dichloroethane, etc.) or the like. When reducing agents which can be used in an aqueous solvent such as sodium borohydride are used, there may be used water and alcohols (e.g., methanol, ethanol, diethylene glycol, etc.). These solvents may be used alone or in combination thereof in appropriate ratios. The reaction temperature is not specifically limited and is preferably about −10° to 100° C.

The reaction time is several minutes to several ten hours.

The compound (VI) obtained by the above reduction can be converted into the compound (II) according to known methods, for example, the method described in Tetrahedron, 46, 7667 (1990), namely by chlorination and hydrolysis.

Further, the compound (VI) can be converted into the compound (III) according to, for example, the method described in J. Am. Chem. Soc., 100, 1558 (1978), namely by action of oxidating agents such as hydrogen peroxide, sodium periodate or the like. The compound (IIa) can be obtained by using the compound (II) and (III) as the starting materials according to the above processes.

According to the present invention, the oxidation of the compound (II') is efficiently carried out by using DMSO and an activating agent to give the compound (VII). Examples of the activating agent include acetic anhydride, a complex of sulfuric anhydride and pyridine, halogen (e.g., chlorine, bromine, iodine, etc.), acetyl halide (e.g., acetyl chloride, etc.), phosphoric anhydride and the like. These activating agents can be used alone or in combination thereof.

When acetic anhydride is used as the activating agent, in order to obtain the compound (VII) selectively, a substantial amount of the oxidizing agent should be firstly formed. Namely, DMSO is firstly activated with acetic anhydride. Then, the compound (II') is added thereto to carry out oxidation. Thus, this reaction is carried out by two stages, i.e., activation of DMSO and oxidation of the compound (II').

The reaction temperature and time of the first stage reaction are of very importance for the selective oxidation. The reaction temperature is about 15° to 150° C., preferably about 25° to 100° C. The reaction time is correlated to the reaction temperature and, when the reaction temperature is relatively low, e.g., 25° C., the reaction time of 3 to 100 hours is required. When the reaction temperature is relatively high, e.g., 80° C., the reaction time is up to 10 hours. Normally, the reaction time of up to 3 hours is sufficient.

The amount of acetic anhydride is also of importance in view of the selectivity of the compound (VII). Normally, acetic anhydride is used in an amount of about 1 to 20 moles, preferably about 2 to 10 moles based on the compound (II').

The reaction temperature of the second stage reaction is about 15° to 150° C., preferably 25° to 100° C. The reaction time is correlated to the reaction temperature and, when the reaction temperature is relatively low, e.g., 25° C. the reaction time of 10 to 30 hours is required. When the reaction temperature is relatively high, e.g., 80° C., the reaction time of 15 minutes to 1 hour is sufficient.

The compound (VII) thus obtained can be isolated and purified by a per se known method such as extraction with a solvent, change of nature of solution, conversion of solvent, salting out, crystallization, recrystallization, chromatography or the like. In particular, when the reaction mixture is added to water, the compound (VII) is crystallized and crystals can be separated by, for example, filtration to isolate the compound (VII).

The compound (VII) can be led to D-biotin according to the method described in JP-B 53-27279 (U.S. Pat. No. 3,740,416), for example, the following reaction steps.

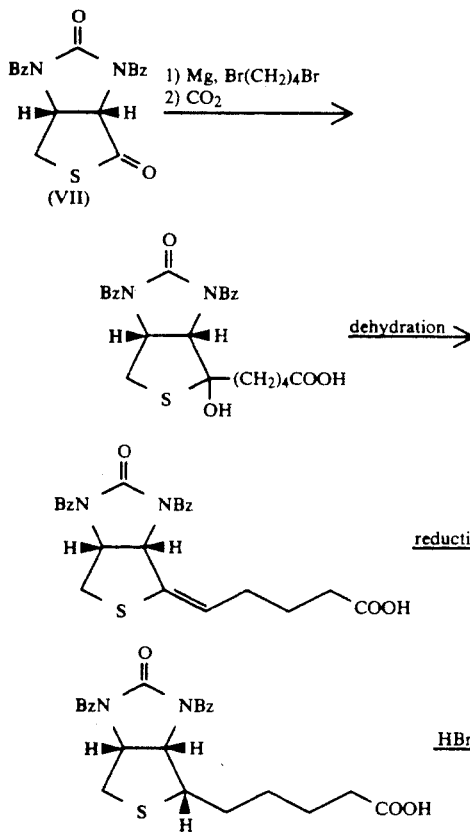

wherein Bz is a benzyl group.

D-biotin is also referred to as vitamin H and is used widely for medicaments and feed additives.

In the above production processes, the starting material (II) can be prepared according to known processes, for example, that described in Tetrahedron, 46, 7677 (1990). The starting material (III) can be prepared according to known processes, for example, that described in J. Am. Chem. Soc., 100, 1558 (1978).

Optically active D-biotin can be prepared readily in high yield and high purity by using the compound (I) of the present invention as the starting material.

In the process of the present invention, the compound (I') and (I'') are contacted with a culture solution of microorganisms or its processed material to obtain the optically active compound (II') or (II'') readily in high yield.

The following examples and reference examples further illustrate the present invention in detail but are not to be construed to limit the scope thereof.

NMR spectra were determined with JNM-GSX 270 (270 MHz) spectrometer (manufactured by Nippon Bunkoh, Japan) by using tetramethylsilane as an internal standard. In the NMR spectra, all the δ values are indicated in terms of ppm. In the mixed solvents, values indicated in parentheses are mixed ratios by volume of each solvent. All the percents are by weight unless otherwise stated.

Symbols in examples represent as follows:

s: singlet, d: doublet, t: triplet, q: quartet, dd: double doublet, m: multiplet, br.: broad, J: coupling constant, Ph: phenyl group, Ac: acetyl group.

The conversion rate from [the compound (Ia)+the compound (Ib)] to [the compound (IIa)+the compound (IIb)] is determined by measuring contents of each component in the reaction mixture by high performance liquid chromatography and by using the data according to the following equation:

Conversion rate (%) =

$$\left( \begin{array}{c} \text{content of the} \\ \text{compounds} \\ [(IIa) + (IIb)] \\ \text{in the reaction mixture} \end{array} \Big/ \begin{array}{c} \text{content of the compounds} \\ [(Ia) + (Ib) + \\ (IIa) + (IIb)] \\ \text{in the reaction mixture} \end{array} \right) \times 100$$

According to the same manner, the conversion rate from [the compound (IIa)+the compound (IIb)] to [the compound (Ia)+the compound (Ib)] is determined by the following equation:

Conversion rate (%) =

$$\left( \begin{array}{c} \text{content of the} \\ \text{compounds} \\ [(Ia) + (Ib)] \\ \text{in the reaction mixture} \end{array} \Big/ \begin{array}{c} \text{content of the compounds} \\ [(Ia) + (Ib) + \\ (IIa) + (IIb)] \\ \text{in the reaction mixture} \end{array} \right) \times 100$$

Specifically, the reaction mixture is extracted with an appropriate organic solvent (e.g., ethyl acetate) and the extract is subjected to high performance liquid chromatography using a chiral column (e.g., CHIRACEL OD, manufactured by Daicel Chemical Industries, Ltd., Japan).

The steric selectivity, i.e., enantiomer excess (e.e.) is calculated from the following equations:

$$e.e.(\%) = \{[(Ia) - (Ib)]/[(Ia) + (Ib)]\} \times 100$$

$$e.e.(\%) = \{[(IIa) - (IIb)]/[(IIa) + (IIb)]\} \times 100$$

EXAMPLE 1

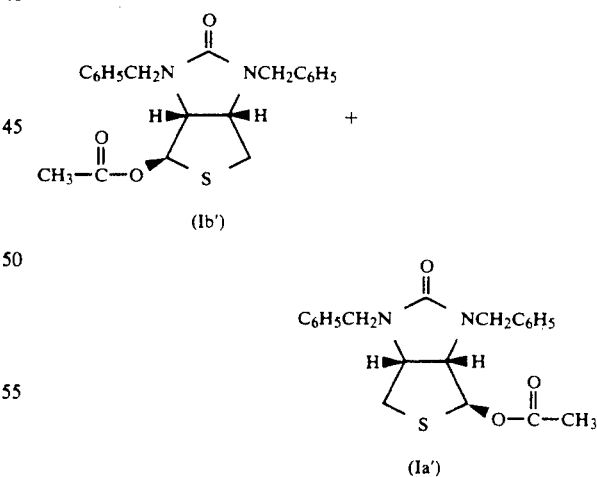

(±)-(3aα, 4α, 6aα)-Tetrahydro-1,3-dibenzyl-4-hydroxy-1H-thieno[3,4-d]imidazol-2(3H)-one (0.5 g) was dissolved in pyridine (2.0 ml) and acetic anhydride (2.0 ml) was added. After stirring at room temperature for 1.5 hours, the solvent was distilled off under reduced pressure. The colorless oil thus obtained was dissolved in a small amount of ether, and n-hexane was added to obtain crystals of (±)-(3aα, 4α, 6aα)-tetrahydro-4-acetoxy-1,3-dibenzyl-1H-thieno[3,4-d]imidazol- 2(3H)-one. Yield: 0.51 g (91%). The structure was confirmed on the basis of melting point, mass spectrum (MS), infrared absorption spectrum (IR), nuclear magnetic resonance spectrum (NMR) and X-ray structural analysis.

mp: 72°-74° C. MS: m/e 382 (M+).

IR (KBr)cm$^{-1}$: 1745, 1700, 1455, 1240, 960, 700.

NMR (CDCl$_3$): 1.96 (3H, s, CH$_3$), 2.96 (1H, d, J=10.2, CH$_2$(endo)S), 3.03 (1H, dd, J=10.2, 3.87, CH$_2$(exo)S), 4.02 (1H, d, J=5.8, CHN), 4.2 (1H, m, CHN), 4.19, 4.24, 4.79, 4.84 (each 1H, d, J=15.4, CH$_2$Ph), 6.02 (1H, s, CHOAc), 7.29 (10H, m, Ph).

EXAMPLE 2

(±)-(3aα, 4α, 6aα) Tetrahydro-1,3-dibenzyl-4-hydroxy-1H-thieno[3,4-d]imidazol-2(3H)-one (5.00 g) was stirred in acetic anhydride (25 ml) and a drop of sulfuric acid was added. After stirring at room temperature for 1 hour, the solvent was distilled off under reduced pressure. The resulting oil was washed with a saturated aqueous solution of sodium bicarbonate and then was dissolved in a small amount of ether. n-Hexane was added thereto to obtain crystals of (±)-(3aα, 4α, 6aα)-tetrahydro-4-acetoxy-1,3-dibenzyl-1H-thieno[3,4-d]imidazol-2(3H)-one (4.00 g, yield: 72%). From the mother liquor, (3aα, 4α, 6aα)-tetrahydro-4-acetoxy-1,3-dibenzyl-1H-thieno[3,4d]imidazol-2(3H)-one (0.93 g, yield: 17%) was obtained.

The IR and NMR values were identical with those obtained in Example 1.

EXAMPLE 3

(±)-(3aα, 5α, 6aα)-Tetrahydro-1,3-dibenzyl-1H-thieno[3,4-d]imidazol-2(3H)-one-5-oxide (200 mg) was dissolved in acetic anhydride (3.0 ml) and stirred at 80° C. for 4 hours. Thereafter, the solution was concentrated under reduced pressure. Diethyl ether was added and washed with an aqueous bicarbonate solution. After drying over anhydrous sodium sulfate, the drying agent was removed by filtration. The filtrate was concentrated under reduced pressure to obtain a crude product, which was then subjected to silica gel chromatography [10 g, n-hexane/ethyl acetate (1:1)] to obtain colorless oil of (±)-(3aα, 6aα)-tetrahydro-4-acetoxy-1,3-dibenzyl-1H-thieno[3,4-d]imidazol-2(3H)-one (206 mg, yield: 92%). According to the NMR analysis of the product, it was confirmed that the 4α and 4β isomers were present in the ratio of 55:45.

EXAMPLE 4

(±)-(3aα, 5α, 6aα)-Tetrahydro-1,3-dibenzyl-1H-thieno[3,4-d]imidazol-2(3H)-one-5-oxide (100 mg) was dissolved in dichloromethane (1.0 ml). Acetic anhydride (0.060 ml) and p-toluenesulfonic acid (28 mg) were added, and the mixture was stirred at room temperature for 17 hours. Thereafter the solvent was distilled off under reduced pressure. Diethyl ether was added to the residue, which was then washed with an aqueous bicarbonate solution. After drying over anhydrous sodium sulfate, the drying agent was removed by filtration. The filtrate was concentrated under reduced pressure to obtain a crude product, which was then subjected to silica gel chromatography [5 g, n-hexane/ethyl acetate (1:1)] to obtain colorless oil of (±)-(3aα, 6aα)-tetrahydro-4-acetoxy-1,3-dibenzyl-1H-thieno[3,4-d]imidazol-2(3H)-one (94 mg, yield: 84%). According to the NMR analysis of the compound, it was confirmed that the 4α and 4β isomers were present in the ratio of 93:7.

EXAMPLE 5

(±)-(3aα, 5α, 6aα)-Tetrahydro-1,3-dibenzyl-1H-thieno[3,4-d]imidazol-2(3H)-one-5-oxide (100 mg) was dissolved in dichloromethane (1.0 ml) which contained hydrogen chloride gas (5.4 mg). Acetic anhydride (0.060 ml) was added and the mixture was stirred at room temperature for 30 hours. Then, the solvent was distilled off under reduced pressure. Diethyl ether was added to the residue, which was then washed with an aqueous bicarbonate solution. After drying over anhydrous sodium sulfate, the drying agent was removed by filtration. The filtrate was concentrated under reduced pressure to obtain a crude product, which was then subjected to silica gel chromatography [5 g, n-hexane/ethyl acetate (1:1)] to obtain colorless oil of (±)-(3aα, 6aα)-tetrahydro-4-acetoxy-1,3-dibenzyl-1H-thieno[3,4-d]imidazol-2(3H)-one (51 mg, yield: 45%). According to the NMR analysis of the product, it was confirmed that the 4α and 4β isomers were present in the ratio of 95:5.

EXAMPLE 6

(±)-(3aα, 5α, 6aα)-Tetrahydro-1,3-dibenzyl-1H-thieno[3,4-d]imidazol-2(3H)-one-5-oxide (100 mg) was dissolved in dichloromethane (1.0 ml). Acetic anhydride (0.060 ml) and phosphoric acid (0.086 ml) were added and the mixture was stirred at room temperature for 24 hours. Then, the solvent was distilled off under reduced pressure. Diethyl ether was added to the residue, which was then washed with an aqueous bicarbonate solution. After drying over anhydrous sodium sulfate, the drying agent was removed by filtration. The filtrate was concentrated under reduced pressure to obtain a crude product, which was then subjected to silica gel chromatography [5 g, n-hexane/ethyl acetate (1:1)] to obtain colorless oil of (±)-(3aα, 6aα)-tetrahydro-4-acetoxy-1,3-dibenzyl-1H-thieno[3,4-d]imidazol-2(3H)-one (100 mg, yield: 89%). According to the NMR analysis of the compound, it was confirmed that the 4α and 4β isomers were present in the ratio of 68:32.

EXAMPLE 7

(±)-(3aα, 5α, 6aα)-Tetrahydro-1,3-dibenzyl-1H-thieno[3,4-d]imidazol-2(3H)-one-5-oxide (100 mg) was dissolved in dichloromethane (1.0 ml). Acetic anhydride (0.060 ml) and sulfuric acid (0.078 ml) were added, and the mixture was stirred at room temperature for 24 hours. Then, the solvent was distilled off under reduced pressure. Diethyl ether was added to the residue, which was then washed with an aqueous bicarbonate solution. After drying over anhydrous sodium sulfate, the drying agent was removed by filtration. The filtrate was concentrated under reduced pressure to obtain a crude product, which was then subjected to silica gel chromatography [5 g, n-hexane/ethyl acetate (1:1)] to obtain colorless oil of (±)-(3aα, 6aα)-tetrahydro-4-acetoxy-1,3-dibenzyl-1H-thieno[3,4-d]imidazol-2(3H)-one (81 mg, yield: 72%). According to the NMR analysis of the compound, it was confirmed that the 4α and 4β isomers were present in the ratio of 93:7.

EXAMPLE 8

(±)-(3aα, 5α, 6aα)-Tetrahydro-1,3-dibenzyl-1H-thieno[3,4-d]imidazol-2(3H)-one-5-oxide (100 mg) was dissolved in dichloromethane (1.0 ml). Acetic anhydride (0.060 ml) and trifluoromethanesulfonic acid (0.129 ml) were added and the mixture was stirred at room temperature for 5 hours. Then, the solvent was distilled off under reduced pressure. Diethyl ether was added to the residue, which was then washed with an aqueous bicarbonate solution. After drying over anhydrous sodium sulfate, the drying agent was removed by filtration. The filtrate was concentrated under reduced pressure to obtain a crude product, which was then subjected to silica gel chromatography [5 g, n-hexane/ethyl acetate (1:1)] to obtain colorless oil of ($\pm$)-(3a$\alpha$, 6a$\alpha$)-tetrahydro-4-acetoxy-1,3-dibenzyl-1H-thieno[3,4-d]imidazol-2(3H)-one (53 mg, yield: 47%). According to the NMR analysis of the compound, it was confirmed that the 4$\alpha$ and 4$\beta$ isomers were present in the ratio of 68:32.

EXAMPLE 9

($\pm$)-(3a$\alpha$, 5$\alpha$, 6a$\alpha$)-Tetrahydro-1,3-dibenzyl-1H-thieno[3,4-d]imidazol-2(3H)-one-5-oxide (100 mg) was dissolved in dichloromethane (1.0 ml). Acetic anhydride (0.060 ml) and Amberlyst 15 (50 mg) were added, and the mixture was stirred at room temperature for 70 hours. Then, the acidic ion exchange resin (Amberlyst 15, manufactured by Organo, Japan) was removed by filtration and the solvent was distilled off under reduced pressure. After drying over anhydrous sodium sulfate, the drying agent was removed by filtration. The filtrate was concentrated under reduced pressure to obtain a crude product, which was then subjected to silica gel chromatography [5 g, n-hexane/ethyl acetate (1:1)] to obtain colorless oil of ($\pm$)-(3a$\alpha$, 6a$\alpha$)-tetrahydro-4-acetoxy-1,3-dibenzyl-1H-thieno[3,4-d]imidazol-2(3H)-one (94 mg, yield: 84%). According to the NMR analysis of the compound, it was confirmed that the 4$\alpha$ and 4$\beta$ isomers were present in the ratio of 93:7.

EXAMPLE 10

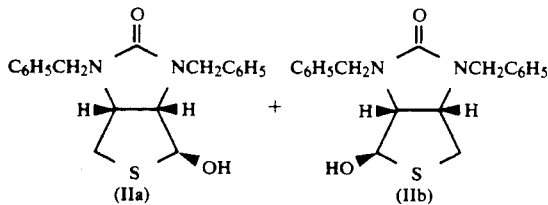

Each bacterium was inoculated into a culture (2 ml, pH 7.2) composed of dextrin (1%), glucose (1%), glycerol (1%), peptone (0.5%), yeast extract (0.5%), meat extract (0.5%), sodium chloride (0.3%) and calcium carbonate (0.5%) (wherein each "%" is w/v %) (hereinafter referred to as A1 medium), and cultivated with shaking at 28° C. for 2 days. To the resulting culture (2 ml) was added 50 μl, 100 μl or 200 μl of a methanol solution of ($\pm$)-(3a$\alpha$, 4$\alpha$, 6a$\alpha$)-tetrahydro-4-acetoxy-1,3-dibenzyl-1H-thieno[3,4-d]imidazol-2(3H)-one (80 mg/ml) obtained in Example 1 so that the substrate concentration became 2 mg/ml, 4 mg/ml or 8 mg/ml, respectively. The culture solution was shaken at 28° C. for 24 hours.

Ethyl acetate (12 ml) was added to the resulting culture, and the mixture was stirred. The ethyl acetate layer was diluted with n-hexane/isopropanol (6:4), and subjected to quantitative analysis by high performance liquid chromatography (HPLC) (detection wavelength: 220 nm) using CHIRACEL OD (manufactured by Daicel Chemical Industries, Ltd., Japan) as the column and n-hexane/isopropanol (6:4) as the mobile phase to determine the starting material and the desired product. Further, the rate of conversion and the ratio of the compounds (IIa) and (IIb) were determined. The results are shown in Table 1.

TABLE 1

| Bacteria | Concentration of substrate (mg/ml) | rate of conversion (%) | (IIa):(IIb) |
|---|---|---|---|
| Acetobacter rancens IFO 3298 | 2 | 16 | 90:10 |
| Bacillus cereus IFO 3003 | 2 | 24 | 8:92 |
| Bacillus megaterium IFO 13498 | 2 | 35 | 2:98 |
| Bacillus megaterium IFO 12108 | 2 | 48 | 18:82 |
| Brevibacterium iodinum IFO 3558 | 2 | 40 | 10:90 |
| Pseudomonas aeruginosa IFO 3445 | 2 | 40 | 10:90 |
| Pseudomonas aeruginosa IFO 3445 | 4 | 30 | 7:93 |
| Pseudomonas aeruginosa IFO 3445 | 8 | 20 | 7:93 |
| Pseudomonas aeruginosa IFO 3447 | 2 | 57 | 16:84 |
| Pseudomonas aeruginosa IFO 3447 | 4 | 47 | 8:92 |
| Pseudomonas aeruginosa IFO 3447 | 8 | 37 | 6:94 |
| Pseudomonas aeruginosa IFO 3448 | 2 | 49 | 7:93 |

FIG. 1 shows the HPLC pattern in the reaction using Paseudomonas aeruginosa IFO 3447 in which the substrate concentration is 4 mg/ml.

EXAMPLE 11

Actinomycetes were inoculated into A1 medium prepared by using the same composition as that in Example 10 and cultivated with shaking at 28° C. for 3 days. To the resulting culture (2 ml) was added 50 μl or 200 μl of a methanol solution of ($\pm$)-(3a$\alpha$, 4$\alpha$, 6a$\alpha$)-tetrahydro-4-acetoxy-1,3-dibenzyl-1H-thieno[3,4-d]imidazol-2(3H)-one (80 mg/ml) so that the substrate concentration became 2 mg/ml or 8 mg/ml, respectively. The culture was subjected to the reaction with shaking at 28° C. for 1 to 24 hours. According to the same manner as that described in Example 10, the rate of conversion and the ratio of the compounds (IIa) and (IIb) were determined. The results are shown in Table 2.

TABLE 2

| Actinomycetes | Concentration of substrate (mg/ml) | Reaction time (hour) | Rate of conversion (%) | (IIa):(IIb) |
|---|---|---|---|---|
| Ampullariella digetata IFO 12512 | 2 | 24 | 19 | 93:7 |
| Streptomyces rochei var. volubilis IFO 12507 | 2 | 1 | 41 | 91:9 |
| Streptomyces rochei var. volubilis IFO 12507 | 2 | 3 | 57 | 80:20 |
| Streptomyces rochei var. volubilis | 8 | 4 | 23 | 88:12 |

TABLE 2-continued

| Actinomycetes | Concentration of substrate (mg/ml) | Reaction time (hour) | Rate of conversion (%) | (IIa):(IIb) |
|---|---|---|---|---|
| IFO 12507 | | | | |

FIG. 2 shows the HPLC pattern in the reaction for 1 hour using *Streptomyces rochei var. volubilis* IFO 12507 in which the substrate concentration is 2 mg/ml.

EXAMPLE 12

Fungi were inoculated in a test tube containing a medium (2 ml) composed of yeast extract (0.3%), meat extract (0.3%), peptone (0.5%) and glucose (0.1%) (wherein each "%" is w/v %), and cultivated with shaking at 28° C. for 3 days. To the resulting culture (2 ml) was added a methanol solution (50 μl) of (±)-(3aα, 4α, 6aα)-tetrahydro-4-acetoxy-1,3-dibenzyl-1H-thieno[3,4-d]imidazol-2(3H)-one (80 mg/ml). The culture solution was subjected to the reaction with shaking at 28° C. for 24 hours. According to the same manner as that described in Example 10, the rate of conversion and the ratio of the compounds (IIa) and (IIb) were determined. The results are shown in Table 3.

TABLE 3

| Fungi | Rate of conversion | (IIa):(IIb) |
|---|---|---|
| *Candida guilliermondii* IFO 14242 | 15 | 12:88 |
| *Trichosporon fermentans* IFO 1199 | 47 | 12:88 |

EXAMPLE 13

*Pseudomonas aeruginosa* IFO 3447 was inoculated in a 200 ml Erlenmeyer flask containing a medium (pH 7.2, 40 ml) composed of dextrin 1%, glucose 1%, glycerol (1%), peptone (0.5%), yeast extract (0.5%), meat extract (0.5%), sodium chloride (0.3%) and calcium carbonate (0.5%) (wherein each "%" is w/v %), and cultivated with shaking at 28° C. for 24 hours. The resulting culture (1 ml) was transferred to 20 ml Erlenmeyer flasks containing a medium having the same composition as above, and cultivated with shaking at 28° C. for 48 hours. To the resulting culture was added (±)-(3aα, 4α, 6aα)-tetrahydro-4-acetoxy-1,3-dibenzyl-1H-thieno[3,4-d]imidazol-2(3H)-one (160 mg) in methanol (2 ml). The mixture was subjected to the reaction with shaking at 28° C. for 18 hours.

This was repeated 13 times. Ethyl acetate was added to the resulting culture, and the mixture was stirred and the ethyl acetate layer was obtained. A part of the ethyl acetate layer was taken and analyzed by HPLC. As a result, the rate of conversion was 40%, and the ratio of the compounds (IIa):(IIb) was 5:95.

The ethyl acetate layer was concentrated to dryness under reduced pressure to obtain a solid (2.32 g). This solid was crystallized from a mixed solvent of ethyl acetate (12 ml) and n-hexane (6 ml) to obtain crystalline (−)-(3aα, 4α, 6aα)-tetrahydro-1,3-dibenzyl-4-hydroxy-1H-thieno[3,4-d]imidazol-2(3H)-one (0.613 g).

mp: 163°–164° C. MS: m/e 340 (M+).

IR (KBr)cm$^{-1}$: 3300, 2930, 1680.

NMR (CDCl$_3$): 1.66 (1H, br s, OH), 2.86 (1H, d, J=12.7, CH$_2$(endo)S), 3.01 (1H, dd, J=12.7, 4.7, CH$_2$(exo)S), 4.21 (1H, dd, C(6a)-H), 4.02 (1H, d, J=7.9, C(3a)-H), 4.75,4.67,4.31,4.21 (each 1H, d, J=15.7, PhCH$_2$), 5.18 (1H, s, CHOH), 7.2–7.4 (10H, m, Ph).

Specific rotation: $[\alpha]_D^{27}$=−68.1° (c=0.78, chloroform).

Then, the mother liquor was concentrated under reduced pressure to obtain oil, which was then subjected to silica gel chromatography [100 g, n-hexane/ethyl acetate (1:1)] to obtain oily (±)-(3aα, 4α, 6aα)-tetrahydro-4-acetoxy-1,3-dibenzyl-1H-thieno[3,4-d]imidazol-2(3H)-one. This oil was dissolved in ethanol (5 ml). Potassium hydroxide (5%) (15 ml) was added and the mixture was stirred at 60° C. for 1.5 hours. Crystals which crystallized upon cooling was filtered off and recrystallized from ethyl acetate (14 ml) and n-hexane(10 ml) to obtain crystals of (+)-(3aα, 4α, 6aα)-tetrahydro-1,3-dibenzyl-4-hydroxy-1H-thieno[3,4-d]imidazol-2(3H)-one (0.597 g).

The melting point, MS, IR, and NMR were in complete agreement with those of the (−) isomer described in Example 13.

Specific rotation: $[\alpha]_D^{27}$=+67.5° (c=0.78, chloroform).

EXAMPLE 14

*Streptomyces rochei var. volubilis* IFO 12507 (see, JP-A 59-183695) was inoculated in a 200 ml Erlenmeyer flask containing a medium (pH 7.2, 40 ml) composed of dextrin (1%), glucose (1%), glycerol (1%), peptone (0.5%), yeast extract (0.5%), meat extract (0.5%), NaCl (10.3%) and calcium carbonate (0.5%), and cultivated with shaking at 28° C. for 3 days. The resulting culture was centrifuged at 10,000 rpm for 10 minutes to obtain culture supernatant. To the culture supernatant (2 ml) was added a dimethylsulfoxide solution (50 μl) of (±)-(3aα, 4α, 6aα)-tetrahydro-4-acetoxy-1,3-dibenzyl-1H-thieno[3,4-d]imidazol-2(3H)-one (80 mg/ml) so that the substrate concentration became 2 mg/ml. The reaction mixture was kept at 28° C. for 1 hour or 2 hours with shaking. Ethyl acetate (2 ml) was added to the reaction mixture after the reaction, and the resulting mixture was stirred. The ethyl acetate layer (100 μl) was taken and concentrated under reduced pressure. The concentrate was diluted with n-hexane/isopropanol (6:4) to determine the starting material and the product by high performance liquid chromatography (HPLC) (detection wavelength: 220 nm) using CHIRACEL 0D (manufactured by Daicel Chemical Industries, Ltd., Japan) as the column and n-hexane/isopropanol (6:1) as the mobile phase. Further, the rate of conversion and the ratio of the compounds (IIa) and (IIb) were determined. The results were shown in Table 4.

TABLE 4

| Reaction time (hour) | Rate of conversion (%) | (IIa):(IIb) |
|---|---|---|
| 1 | 37 | 95:5 |
| 2 | 53 | 92:8 |

EXAMPLE 15

*Streptomyces rochei var. volubilis* IFO 12507 was inoculated in a 200 ml Erlenmeyer flask containing a medium (pH 7.2, 40 ml) composed of dextrin (1%), glucose (1%), glycerol (1%), peptone (0.5%), yeast extract (0.5%), meat extract (0.5%), NaCl (0.3%) and calcium carbonate (0.5%) (wherein each "%" is w/v %), and cultivated with shaking at 28° C. for 3 days. The resulting culture (4 ml) was transferred to a 1 liter Erlenmeyer flask containing the above medium (200 ml), and the microorganism was cultivated with shaking at 28° C. for 3 days. The resulting solution was centrifuged to obtain the culture supernatant.

In dimethyl sulfoxide (40 ml) was dissolved (±)-(3aα, 4α, 6aα)-tetrahydro-4-acetoxy-1,3-dibenzyl-1H-thieno[3,4-d]imidazol-2(3H)-one (3.2 g). The solution was added to the culture supernatant (1.6 liters) obtained by the above method on a large scale, and the mixture was subjected to the reaction at 28° C. for 1 hour with shaking.

The rate of conversion and the ratio of the compounds (IIa) and (IIb) were determined by the same manner as that described in Example 14. As a result, they were 27.7% and 96:4, respectively.

The reaction mixture after the reaction was extracted with ethyl acetate (1.6 liters) and the remaining aqueous layer was extracted with ethyl acetate (900 ml) twice.

The resulting ethyl acetate layer (ca. 3.5 liters) was concentrated under reduced pressure, and the concentrate was dissolved in ethyl acetate (500 ml). The solution was washed with water (500 ml) and saturated brine (500 ml) and concentrated under reduced pressure to obtain yellow oil (3.78 g).

The resulting oil (3.78 g) was dissolved in acetone (7.0 ml) by heating. Crystallization began upon cooling at 0° C. After about 1.5 hours, crystals (344 mg) were obtained by filtration. Further, the mother liquor was allowed to stand to obtain additional crystals (51 mg).

Each value of the melting point, MS, IR and NMR was in complete agreement with those of the compound (IIb) of Example 13.

Specific rotation $[\alpha]_D^{30} = +62.4°$ (c=0.78, chloroform).

EXAMPLE 16

A medium (500 ml) composed of glucose (3.0%), Profro (trade name, Trader Oil Co. Ltd., Japan) (1.0%), corn steep liquor (3.5%), magnesium sulfate (0.02%), dipotassium hydrogenphosphate (0.1%), soybean oil (0.05%), calcium carbonate (1.5%) (wherein each "%" is w/v %) was adjusted to pH 7.0 with 20% aqueous sodium hydroxide solution, and then distributed in 2 liter Sakaguchi flasks. The flasks were cotton plugged, and then sterilized. A slant culture of *Streptomyces rochei var. volubilis* IFO 12507 (ATCC 21250) (JP-A 59-183695) was inoculated into the sterilized medium and then cultivated at 28° C. for 24 hours on a reciprocating shaker (83 spm). A medium (30 liters) having the same composition as above was prepared in a 50 liter fermenter and sterilized. The above culture (500 ml) in Sakaguchi flasks was inoculated, and cultivated at 24° C. for 24 hours at an aeration rate of 1 VVM (aeration volume per unit volume per minute) with stirring at a rotation rate of 150 rpm to prepare a seed medium. A culture medium (100 liters) composed of glycerin (10%), Profro (trade name, Trader Oil Co., Ltd., Japan) (2.0%), corn steep liquor (0.5%), polypeptone (1.0%), ferrous sulfate (0.1%), soybean oil (0.01%) and β-cyclodextrin (2.0%) (wherein each "%" is w/v %) was prepared in a 200 liter fermenter and adjusted to pH 7.0 with 20% aqueous sodium hydroxide solution, and then steam-sterilized at 120° C. for 20 minutes. The above seed medium (5 liters) was transferred to the sterilized medium and cultivated at 24° C. for 96 hours at an aeration rate of 1 VVM with stirring at a rotation rate of 165 rpm.

The culture (60 liters) thus obtained was taken and water (20 liters) and Hyflo Super Cel (manufactured by John Manville Sales Corp., U.S.A.) (2 kg) were added thereto for filtration. The filtrate (70 liter) was obtained. The filtrate (10 liters) was taken into a 60 liter container, and ethanol (30 liters) was added thereto. The resulting mixture was thoroughly stirred by using a stirring bar. The mixture was allowed to stand at 5° C. for 12 hours to form precipitate of protein. The supernatant was removed by a siphon to obtain cloudy precipitate. The precipitate was subjected to refrigerating centrifugation at 5° C. at 2,000×g to remove water as much as possible. Ethanol was added for washing. Centrifugation was carried out under the same conditions. The precipitate was collected and vacuum drying was carried out at 50 mmHg and 10° C. for 24 hours to obtain a powdery enzyme (200 g).

The above enzyme was dissolved in a 0.1M phosphate buffer (pH 7.0) to obtain solutions having various concentrations. To the resulting solution (2 ml) was added a dimethyl sulfoxide solution (50 µl) containing (±)-(3aα, 4α, 6aα)-tetrahydro-4-acetoxy-1,3-dibenzyl-1H-thieno[3,4-d]imidazol-2(3H)-one (80 mg/ml) so that the substrate concentration became 2 mg/ml. The reaction mixture was kept with shaking at 28° C. for 1 hour. Then the rate of conversion and the ratio of the compounds (IIa) and (IIb) were determined. The results are shown in Table 5.

TABLE 5

| Enzyme concentration (mg/ml) | Rate of conversion (%) | (IIa):(IIb) |
| --- | --- | --- |
| 0 | 0 | — |
| 0.25 | 26 | 96:4 |
| 0.5 | 37 | 89:11 |
| 1.0 | 48 | 84:16 |

EXAMPLE 17

*Pseudomonas aeruginosa* IFO 3447 was inoculated into a medium (pH 7.2, 40 ml) composed of dextrin (1%), glucose (1%), glycerol (1%), peptone (0.5%), yeast extract (0.5%), meat extract (0.5%), NaCl (0.3%) and calcium carbonate (0.5%) (wherein each "%" is w/v %), and cultivated with shaking at 28° C. for 24 hours. The resulting culture (1 ml) was transferred to a 200 ml Erlenmeyer flask containing the same medium (40 ml) as above and cultivated with shaking at 28° C. for 48 hours.

(±)-(3aα, 4α, 6aα)-Tetrahydro-4-acetoxy-1,3-dibenzyl-1H-thieno[3,4-d]imidazol-2(3H)-one (1.04 g) in methanol (13 ml) was added to the culture solution obtained by the above method (total 520 ml) and the mixture was subjected to the reaction with shaking at 28° C. for 24 hours.

Ethyl acetate (1 liter) was added to the resulting reaction mixture. The mixture was stirred and the ethyl acetate layer was obtained. A part of the reaction mixture was taken and analyzed by HPLC. As a result, the rate of conversion was 53% and the ratio of the compounds (IIa) and (IIb) was 15:85.

The ethyl acetate layer was concentrated under reduced pressure to dryness to obtain oil. The oil was subjected to silica gel chromatography [80 g, n-hexane/ethyl acetate (1:1)] to obtain oily (±)-(3aα, 4α, 6aα)-tetrahydro-4-acetoxy-1,3-dibenzyl-1H-thieno[3,4-d]imidazol-2(3H)-one. This was dissolved in a small amount of diethyl ether. n-Hexane was added to the solution and the mixture was allowed to stand to obtain crystals (222 mg).

The melting point, MS, IR and NMR were in complete agreement with those of the racemate in Example 1.

Specific rotation $[\alpha]_D^{29} = +110°$ (c=0.76, chloroform).

In order to determine the optical purity of the crystals, the crystals were hydrolyzed by the method described in Example 13 and led to the compound (II), which was analyzed by HPLC. As a result, it was found that the crystals were optically pure.

EXAMPLE 18

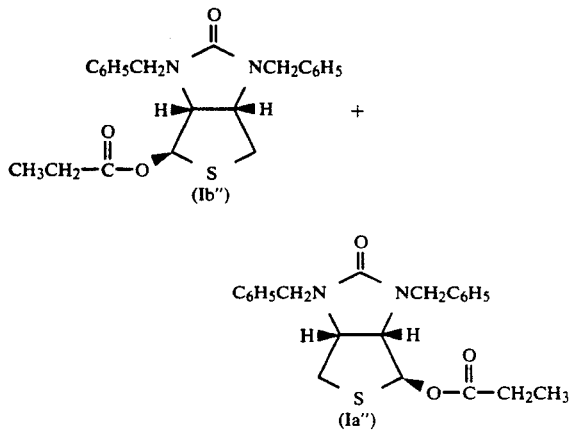

(±)-(3aα, 4α, 6aα)-Tetrahydro-1,3-dibenzyl-4-hydroxy-1H-thieno[3,4-d]imidazol-2(3H)-one (0.50 g) was dissolved in pyridine (2.0 ml) and propionic anhydride (2.0 ml) was added. The mixture was stirred at room temperature for 1 hour and then the solvent was distilled off under reduced pressure. The oil thus obtained was dissolved in a small amount of toluene. The solution was washed successively with an aqueous sodium bicarbonate solution and then water. The solvent was distilled off under reduced pressure and n-pentane was added to obtain crystals of (±)-(3aα, 4α, 6aα)-tetrahydro-1,3-dibenzyl-4-propionyloxy-1H-thieno[3,4-d]imidazol-2(3H)-one. The yield was 0.46 g (78%). The structure was confirmed on the basis of IR and NMR.

IR (KBr)cm$^{-1}$: 1740, 1690, 1475, 1455, 1245.

NMR (CDCl$_3$): 1.07 (3H, t, J=7.5, CH$_3$), 2.22 (2H, q, J=7.5, CH$_2$CH$_3$), 2.95 (2H, m, CH$_2$S), 3.99 (1H, d, J=7.8, C(3a)-H), 4.18, 4.24, 4.79, 4.85 (each 1H, d, J=15.4, CH$_2$Ph), 4.2 (1H, m, C(6a)-H), 6.05 (1H, s, C(4)-H), 7.2-7.3 (10H, m, Ph).

EXAMPLE 19

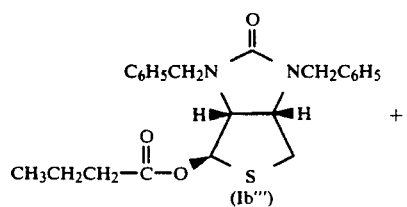

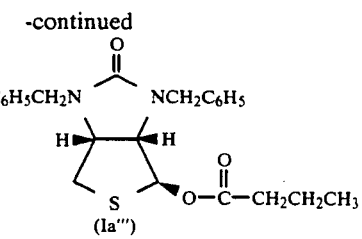

(±)-(3aα, 4α, 6aα)-Tetrahydro-1,3-dibenzyl-4-hydroxy-1H-thieno[3,4-d]imidazol-2(3H)-one (340 mg) was dissolved in dichloromethane (5.0 ml) and triethylamine (0.209 ml) and butyryl chloride (0.154 ml) were added. The mixture was stirred at room temperature for 1.5 hour. The solvent was distilled off. Then, ether was added and insoluble materials were removed. The filtrate was concentrated to obtain oil, which was then purified by silica gel chromatography [n-hexane/ethyl acetate (2:1)] to obtain crystals of (±)-(3aα, 4α, 6aα)-tetrahydro-4-butyryloxy-1,3-dibenzyl-1H-thieno[3,4-d]imidazol-2(3H)-one (147 mg, yield: 36%). The structure was confirmed on the basis of IR and NMR.

IR (KBr)cm$^{-1}$: 1750, 1690, 1480, 1460, 1250.

NMR (CDCl$_3$): 0.89 (3H, t, J=7.3, CH$_3$), 1.58 (2H, m, J=6.9, CH$_2$), 2.18 (2H, t, J=6.9, COCH$_2$), 2.99 (2H, m, CH$_2$S), 3.98 (1H, d, J=7.8, C(3a)-H), 4.18, 4.23, 4.80, 4.87 (each 1H, d, J=15.3, CH$_2$Ph), 4.2 (1H, m, C(6a)-H), 6.06 (1H, s, C(4)-H), 7.2-7.3 (10H, m, Ph).

EXAMPLE 20

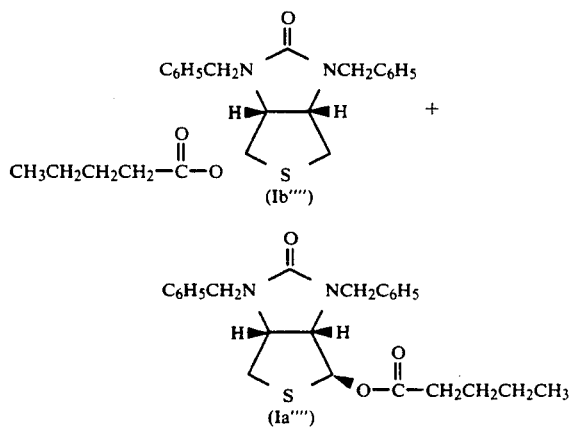

(±)-(3aα, 4α, 6aα)-Tetrahydro-1,3-dibenzyl-4-hydroxy-1H-thieno[3,4-d]imidazol-2(3H)-one (340 mg) was dissolved in diethyl ether (5.0 ml), and triethylamine (0.209 ml) and valeryl chloride (0.198 ml) were added. The mixture was stirred at room temperature for 1.5 hour. Then, the solvent was distilled off to obtain oil, which was then purified by silica gel chromatography [n-hexane/ethyl acetate (2:1)] to obtain colorless oil of (±)-(3aα, 4α, 6aα)-tetrahydro-1,3-dibenzyl-4-valeryloxy-1H-thieno[3,4-d]imidazol-2(3H)-one (111 mg, yield: 26%). The structure was confirmed on the basis of IR and NMR.

IR (KBr)cm$^{-1}$: 1735, 1700, 1450, 1240.

NMR (CDCl$_3$): 0.87 (3H, t, J=6.4, CH$_3$), 1.16-1.62 (4H, m, CH$_2$CH$_2$), 2.21 (2H, t, J=7.4, OCOCH$_2$), 3.98 (1H, d, J=7.9, C(3a)-H), 4.19, 4.22, 4.80, 4.87 (each 1H, d, J=15.4, CH$_2$Ph), 4.2 (1H, m, C(6a)-H), 6.06 (1H, s, C(4)-H), 7.21-7.36 (10H, m, Ph).

MS: m/e 425 (MH$^+$).

EXAMPLE 21

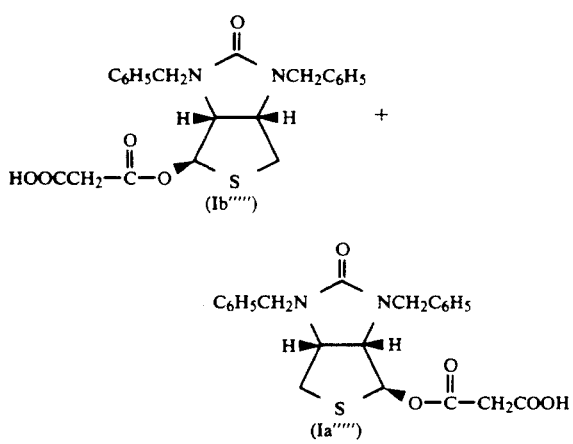

(±)-(3aα, 4α, 6aα)-Tetrahydro-1,3-dibenzyl-4-hydroxy-1H-thieno[3,4-d]imidazol-2(3H)-one (340 mg) and Meldrum's acid (144 mg) were dissolved in toluene (1.0 ml) and the mixture was warmed to 100° C. After 1.5 hours, toluene (5.0 ml) and an aqueous solution (5.0 ml) of sodium bicarbonate were added. The aqueous layer was taken, made weakly acidic with dil. hydrochloric acid and extracted with ether. The ether layer was concentrated under reduced pressure to obtain oil of (±)-(3aα, 4α, 6aα)-tetrahydro-1,3-dibenzyl-4-malonyloxy-1H-thieno[3,4-d]imidazol-2(3H)-one (279 mg, yield: 65%). The structure was confirmed on the basis of IR, MR and MS.

IR (KBr)cm$^{-1}$: 3420, 2930, 1750, 1730, 1700, 1660, 1455, 1245.

NMR (CDCl$_3$): 2.91 (2H, m, CH$_2$S), 3.29 (2H, s, CH$_2$COO), 4.05 (1H, d, J=8.0, C(3a)-H), 4.18, 4.26, 4.73, 4.76 (each 1H, d, J=15.4, CH$_2$Ph), 7.12–7.28 (10H, m, Ph).

MS: m/e 427 (MH$^+$).

EXAMPLE 22

*Pseudomonas aeruginosa* IFO 3447 was inoculated in a 200 ml Erlenmeyer flask containing a medium (pH 7.2, 40 ml) composed of dextrin (1%), glucose (1%), glycerol (1%), peptone (0.5%), yeast extract (0.5%), meat extract (0.5%), NaCl (0.3%) and calcium carbonate (0.5%) and cultivated with shaking at 28° C. for 48 hours. The methanol solution of the compound (I) (80 mg/ml) obtained in Example 1, 18, 19 or 20 was added to the resulting culture (2 ml). The culture thus obtained was kept at 28° C. for 23 hours with shaking. After the reaction, the rate of conversion of the reaction and the ratio of the compounds (IIa) and (IIb) were determined according to the same manner as that described in Example 14. The results are shown in Table 6.

TABLE 6

| Substrate R = | Substrate concentration (mg/ml) | Rate of conversion (%) | (IIa):(IIb) |
|---|---|---|---|
| CH$_3$ | 2 | 55 | 18:82 |
| CH$_3$ | 4 | 50 | 10:90 |
| C$_2$H$_5$ | 2 | 57 | 20:80 |
| C$_3$H$_7$ | 2 | 37 | 43:57 |
| C$_4$H$_9$ | 2 | 42 | 17:83 |

EXAMPLE 23

The reaction mixture obtained by hydrolysis of (±)-(3aα, 4α, 6aα)-tetrahydro-4-acetoxy-1,3-dibenzyl-1H-thieno[3,4-d]imidazol-2(3H)-one (3.36 g) with *Pseudomonas aeruginosa* IFO 3447 was extracted with ethyl acetate. The extract was concentrated under reduced pressure to dryness, and subjected to quantitative analysis by HPLC. As a result, it was found that it contained (+)-(3aα, 4α, 6aα)-tetrahydro-4-hydroxy 1,3-dibenzyl-1H-thieno[3,4-d]imidazol-2(3H)-one (0.789 g, the ratio of the compounds (IIa) and (IIb)=96:4) and (±)-(3aα, 4α, 6aα)-tetrahydro-4-acetoxy-1,3-dibenzyl-1H-thieno[3,4-d]imidazol-2(3H)-one (2.30 g). Then the concentrate was dissolved in acetone (7.0 ml) under heating and cooled to obtain (+)-(3aα, 4α, 6aα)-tetrahydro-4-hydroxy-1,3-dibenzyl-1H-thieno[3,4-d]imidazol-2(3H)-one (0.410 g, the ratio of the compounds (IIb) and (IIa)=97:3).

EXAMPLE 24

(−)-(3aα, 4α, 6aα)-Tetrahydro-4-acetoxy-1,3-dibenzyl-1H-thieno[3,4-d]imidazol-2(3H)-one (5.0 g) was dissolved in ethanol (25 ml), and 5% potassium hydroxide (75 ml) was added thereto. The resulting mixture was heated at 60° C. for 1.5 hours. Crystals crystallized upon cooling were filtered off and dried to obtain (−)-(3aα, 4α, 6aα)-tetrahydro-4-hydroxy-1,3-dibenzyl-1H-thieno[3,4-d]imidazol-2(3H)-one (4.36 g, yield: 98%).

EXAMPLE 25

(−)-(3aα, 4α, 6aα)-Tetrahydro-4-hydroxy-1,3-dibenzyl-1H-thieno[3,4-d]imidazol-2(3H)-one (1.50 g) was stirred in dichloromethane (50 ml) at 0° C. Phosphorus trichloride (0.225 ml) was added dropwise thereto. The reaction was continued at room temperature for 90 minutes, and then the solvent was distilled off under reduced pressure. Diethylene glycol dimethyl ether (30 ml) was added to the residue, and the mixture was cooled to 0° C. Sodium borohydride (0.85 g) was added thereto and reacted at 80° C. for 3 hours. Then, the reaction mixture was poured into ice water. The precipitated crystals were filtered off and dried to obtain (3aα, 4α, 6aα)-tetrahydro-1,3-dibenzyl-1H-thieno[3,4-d]imidazol-2(3H)-one (1.37 g, yield: 96%).

EXAMPLE 26

(−)-(3aα, 4α6aα)-Tetrahydro-4-hydroxy-1,3-dibenzyl-1H-thieno[3,4-d]imidazol-2(3H)-one (1.50 g) was stirred in dichloromethane (50 ml) at 0° C. Sulfuryl chloride (0.485 ml) was added dropwise thereto. The reaction was continued at room temperature for 90 minutes, and then the solvent was distilled off under reduced pressure. Diethylene glycol dimethyl ether (50 ml) was added to the residue and the mixture was cooled to 0° C. Sodium borohydride (1.41 g) was added thereto and reacted at 80° C. for 3 hours. Then, the reaction mixture was poured into ice water. The precipitated crystals were filtered off and dried to obtain (3aα, 6aα)-tetrahydro-1,3-dibenzyl-1H-thieno[3,4-d]imidazol-2(3H)-one (1.36 g, yield: 95%).

EXAMPLE 27

(−)-(3aα, 4α, 6aα)-Tetrahydro-4-hydroxy-1,3-dibenzyl-1H-thieno[3,4-d]imidazol-2(3H)-one (1.5 g) was stirred in dichloromethane (50 ml) at 0° C. The reaction was continued at room temperature for 30 minutes while hydrogen chloride gas was introduced. Then, the solvent was distilled off under reduced pressure. Chloroform (50 ml) and palladium supported on carbon (0.25 g) were added to the the resulting residue, and catalytic hydrogenation was carried out at hydrogen pressure of 50 kg/cm² at room temperature for 7 hours. After the catalyst was filtered off, the filtrate was concentrated under reduced pressure to obtain crystals of (3aα, 6aα)-tetrahydro-1,3-dibenzyl-1H-thieno[3,4-d]imidazol-2(3H)-one (0.89 g, yield: 63%). Further, the mother liquor was concentrated to obtain crystals (0.17 g, yield: 12%).

EXAMPLE 28

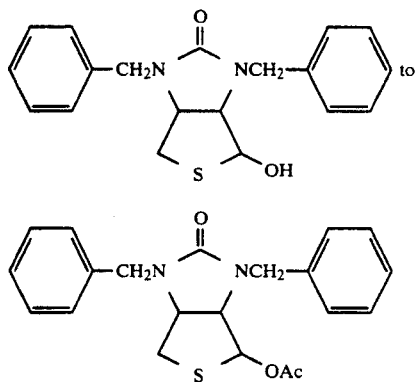

(±)-(3aα, 4α, 6aα)-Tetrahydro-1,3-dibenzyl-4-hydroxy-1H-thieno[3,4-d]imidazol-2(3H)-one (4.0 mg) was dissolved in benzene (2.0 ml), and to the solution were added a commercially available immobilized lipoprotein lipase (manufactured by Toyo Boseki Kabushiki Kaisha, Japan) (40 mg) and vinyl acetate (20 μl). The mixture was stirred at 37° C. for 20 hours. The resulting reaction mixture was diluted with n hexane/isopropanol (6:4) and analyzed by HPLC under the same conditions as described above. The conversion rate was 55% and the ratio of the compounds (IIa) and (IIb) was 99:1. The HPLC pattern is shown in FIG. 3.

EXAMPLE 29

(±)-(3aα, 4α, 6aα)-Tetrahydro-1,3-dibenzyl-4-hydroxy-1H-thieno[3,4-d]imidazol-2(3H)-one (1.0 g) was dissolved in toluene (500 ml) and to the solution were added a commercially available immobilized lipoprotein lipase (manufactured by Toyo Boseki kabushiki Kaisha, Japan) (2.5 g), vinyl acetate (1.0 ml) and molecular sieves 4A 1/16 (5.0 g). The mixture was stirred at 37° C. for 16 hours and the reaction mixture was filtered through membrane filter (pore size: 0.45 μm, manufactured by Advantech, Japan) to remove the immobilized lipoprotein lipase and molecular sieves. The filtrate was analyzed by HPLC. As a result, the conversion rate was 54% and the ratio of the compounds (IIa) and (IIb) was 99.5:0.5. No peak of (−)-(3aα, 4α, 6aα)-tetrahydro-1,3-dibenzyl-4-hydroxy-1H-thieno[3,4-d]imidazol-2(3H)-one was observed. The HPLC pattern is shown in FIG. 4.

Then, the reaction mixture was concentrated under reduced pressure and crystals precipitated were filtered off to obtain (+)-(3aα, 4α, 6aα)-tetrahydro-1,3-dibenzyl-4-hydroxy-1H-thieno[3,4-d]imidazol-2(3H)-one (344 mg, conversion rate: 33.4%, the ratio of the compounds (IIa) and (IIb)=99.9:0.1). The structure was confirmed by mp, IR, NMR and specific rotation.

mp: 166°-168° C.

IR (KBr) cm⁻¹: 3300, 1680.

NMR (CDCl₃): 1.7 (1H, br, s, OH), 2.86 (1H, d, J=12.7, C(6)-H), 3.01 (1H, dd, J=12.7, 4.7, C(6)-H), 4.02 (1H, d, J=7.9, C(3a)-H), 4.21 (1H, dd, J=7.9, 4.6, C(6a)-H), 4.21, 4.32, 4.66, 4.74 (each 1H, d, J=15.5, NCH₂), 5.18 (1H, s, C(4)-H), 7.2-7.4 (10H, m, Ph).

Specific rotation: $[\alpha]_D^{27} = +71.7$ (c=0.87, chloroform).

Further, the mother liquor was concentrated to obtain oil and the oil was purified by subjecting it to silica gel chromatography [n-hexane/ethyl acetate (2:1)] to obtain (+)-(3aα, 4α, 6aα)-tetrahydro-1,3-dibenzyl-4-hydroxy-1H-thieno[3,4-d]imidazol-2(3H)-one (87 mg, conversion rate: 8.7%, the ratio of the compounds (Ia) and (Ib)=99.0:1.0) and (−)-(3aα, 4α, 6aα)-tetrahydro-1,3-dibenzyl-4-acetoxy-1H-thieno[3,4-d]imidazol-2(3H)-one (600 mg, conversion rate: 53.4%).

EXAMPLE 30

Dimethylsulfoxide (250 ml) and acetic anhydride (46.3 ml) were mixed and the mixture was warmed at 50° C. for 1 hour. Then, to the mixture was added (±)-(3aα, 4α, 6aα)-tetrahydro-1,3-dibenzyl-4-hydroxy-1H-thieno[3,4-d]imidazol-2(3H)-one (25 g) and the mixture was stirred at the same temperature for 1.5 hours. The reaction mixture was poured into ice-water (1500 ml) and crystals precipitated were collected by filtration. When the product was analyzed by HPLC, (±)-(3aα, 6aα)-tetrahydro-1,3-dibenzyl-1H-thieno[3,4-d]imidazol-2(3H), 4-dione (82.4%) and (3aα,4α, 6aα)-tetrahydro-1,3-dibenzyl-4-acetoxy-1H-thieno[3,4-d]imidazol-2(3H)-one (9.1%) were produced. The crystals were recrystallized from ethyl acetate to isolate (±)-(3aα, 6aα)-tetrahydro-1,3-dibenzyl-1H-thieno[3,4-d]imidazol-2(3H), 4-dione (18.18 g, 73.2%), mp 125°-126° C.

EXAMPLE 31

Dimethylsulfoxide (10 ml) and acetic anhydride (1.85 ml) were mixed and the mixture was stirred at 50° C. for 1 hour. Then, to the mixture was added (±)-(3aα, 4α, 6aα)-tetrahydro-1,3-dibenzyl-4-hydroxy-1H-thieno[3,4-d]imidazol-2(3H)-one (1.0 g) and the mixture was stirred at the same temperature for 3 hours. The reaction mixture was poured into ice-water (100 ml) and crystals precipitated were collected by filtration. When the product was analyzed by HPLC, (±)-(3aα, 6aα)-tetrahydro-1,3-dibenzyl-1H-thieno[3,4-d]imidazol-2(3H), 4-dione (81.4%) and (±)-(3aα, 4α, 6aα)-tetrahydro-1,3-dibenzyl-4-acetoxy-1H-thieno[3,4-d]imidazol-2(3H)-one (3.7%) were produced.

EXAMPLE 32

Dimethylsulfoxide (10 ml) and acetic anhydride (1.85 ml) were mixed and the mixture was heated at 80° C. for 15 minutes. Then, to the mixture was added (±)-(3aα, 4α, 6aα)-tetrahydro-1,3 dibenzyl-4-hydroxy-1H-thieno[3,4-d]imidazol-2(3H)-one (1.0 g) and the mixture was stirred at the same temperature for 15 minutes. The reaction mixture was poured into ice-water (100 ml) and crystals precipitated were collected by filtration. When the product was analyzed by HPLC, (±)-(3aα, 6aα)-tetrahydro-1,3-dibenzyl-1H-thieno[3,4-d]imodazol-2(3H), 4-dione (78.0%) and (±)-(3aα, 4α, 6aα)-tetrahydro-1,3-dibenzyl-4-acetoxy-1H-thieno[3,4-d]imidazol-2(3H)-one (7.1%) were produced.

EXAMPLE 33

Dimethylsulfoxide (10 ml) and acetic anhydride (0.83 ml) were mixed and the mixture was stirred at 50° C. for 1 hour. Then, to the mixture was added (±)-(3aα, 4α, 6aα)-tetrahydro-1,3-dibenzyl-4-hydroxy-1H-thieno[3,4-d]imidazol-2(3H)-one (1.0 g) and the mixture was stirred at 25° C. for 17 hours. The reaction mixture was poured into ice-water (100 ml) and extracted with dichloromethane. When the extract was analyzed by HPLC, (±)-(3aα, 6aα)-tetrahydro-1,3-dibenzyl-1H-thieno[3,4-d]imidazol-2(3H), 4-dione (78.1%) and (±)-(3aα, 4α, 6aα)-tetrahydro-1,3-dibenzyl-4-acetoxy-1H-thieno[3,4-d]imidazol-2(3-one (7.8%) were produced.

EXAMPLE 34

(±)-(3aα, 4α, 6aα)-Tetrahydro-1,3-dibenzyl-4-hydroxy-1H-thieno[3,4-d]imidazol-2(3H)-one (1.0 g) was dissolved in dimethylsulfoxide (7.5 ml) and to the solution was added trimethylamine (3.35 g). The mixture was cooled to 17° to 19° C. and dissolved with stirring in dimethylsulfoxide (7.5 ml). Sulfur trioxide-pyridine complex (1.52 g) was added dropwise thereto. The mixture was stirred at the same temperature for 45 minutes and poured into water (100 ml). The mixture was adjusted to pH 4.5 with 10% hydrochloric acid. After stirring for one hour, the crystals precipitated were filtered off, washed with water and dried to obtain (±)-(3aα, 6aα)-tetrahydro-1,3-dibenzyl-1H-thieno[3,4-d]imidazol-2(3H), 4-dione (0.82 g, yield: 82.5%).

REFERENCE EXAMPLE 1

Acetone (5.00 ml) was added to (±)-(3aα, 4α, 6aα)-tetrahydro-1,3-dibenzyl-4-hydroxy-1H-thieno[3,4-d]imidazol-2(3H)-one (0.500 g) and (±)-(3aα, 4α, 6aα)-tetrahydro-4-acetoxy-1,3-dibenzyl-1H-thieno[3,4-d]imidazol-2(3H)-one (0.500 g), which were then dissolved at 50° C. The solution was cooled to 0° C. for crystallization. The yield of the resulting crystals was 0.425 g (85%). The nuclear magnetic resonance spectrum and infrared absorption spectrum thereof were in complete agreement with those of (±)-(3aα, 4α, 6aα)-tetrahydro-4-hydroxy-1,3-dibenzyl-1H-thieno[3,4-d]imidazol-2(3H)-one. (±)-(3aα, 4α, 6aα)-Tetrahydro-4-acetoxy-1,3-dibenzyl-1H-thieno[3,4-d]imidazol-2(3H)-one was not found at all in the crystals.

REFERENCE EXAMPLE 2

Acetone (5.00 ml) was added to (±)-(3aα, 4α, 6aα)-tetrahydro-4-hydroxy-1,3-dibenzyl-1H-thieno[3,4-d]imidazol-2(3H)-one (0.200 g) and (±)-(3aα, 4α, 6aα)-tetrahydro-4-acetoxy-1,3-dibenzyl-1H-thieno[3,4-d]imidazol-2(3H)-one (0.800 g), which were then dissolved at 50° C. The solution was cooled to 0° C. for crystallization. The yield of the resulting crystals was 0.13 g (65%). The nuclear magnetic resonance spectrum and infrared absorption spectrum thereof were in complete agreement with those of (±)-(3aα, 4α, 6aα)-tetrahydro-4-hydroxy-1,3-dibenzyl-1H-thieno[3,4-d]imidazol-2(3H)-one. (±)-(3aα, 4α, 6aα)-Tetrahydro-4-acetoxy-1,3-dibenzyl-1H-thieno[3,4-d]imidazol-2(3H)-one was not found at all in the crystals.

REFERENCE EXAMPLE 3

Magnesium (0.90 g) was added to tetrahydrofuran (5.3 ml) and the mixture was stirred. To the mixture was added several drops of 1,2-dichloroethane and the mixture was warmed to 42° C. to start the reaction. After cooling to 35° C., 1,4-dichlorobutane (2.4 g) and tetrahydrofuran (10 ml) were slowly added dropwise and the mixture was stirred at the same temperature for 3 hours and then cooled to −50° C. To the mixture were added dropwise (+)-(3aα, 6aα)-tetrahydro-1,3-dibenzyl-1H-thieno[3,4-d]imidazol-2(3H), 4-dione (2.1 g) and tetrahydrofuran (20 ml). After stirring at the same temperature for 1 hour, $CO_2$ was bubbled through the mixture at −50° C. for 30 minutes. 10% Aqueous hydrogen chloride solution (40 ml) was added dropwise to the mixture at 10° C. The mixture was extracted with toluene. To this was added conc. sulfuric acid (0.06 g) and the mixture was stirred at 80° C. for 1 hour. The reaction mixture was cooled, washed with saturated brine and dried over sodium sulfate. The dried mixture was concentrated to obtain oil. The oil was dissolved in 5% aqueous potassium hydroxide solution (40 ml) and washed with diethyl ether. After neutralizing with 20% sulfuric acid, the mixture was extracted with ethyl acetate. The extract was concentrated under reduced pressure to obtain oil. To the oil was added diethyl ether to obtain crystals of (+)-(3aα, 6aα)-tetrahydro-1,3-dibenzyl-2-[ω-carboxybutylidene)-1H-thieno[3,4-d]imidazol-2(3H)-one (2.14 g).

mp: 87° C.

Specific rotation: $[\alpha]_D = +222$ (c=1.0, methanol).

(+)-(3aα, 6aα)-Tetrahydro-1,3-dibenzyl-4-(ω-carboxybutylidene)-1H-thieno[3,4-d]imidazol-2(3H)-one (1.80 g) and isopropanol (100 ml) were placed in a 200 ml autoclave and reduction was carried out at hydrogen pressure of 50 kg/cm² at 50° C. for 3 hours. After cooling, the catalyst was filtered off and the mixture was concentrated under reduced pressure to obtain (−)-(3aα, 6aα)-tetrahydro-1,3-dibenzyl-4-(ω-carboxybutyl)-1H-thieno[3,4-d]imidazol-2(3H)-one (1.59 g).

mp: 93° C.

Specific rotation: $[\alpha]_D^{22} = -26.6$ (c=1.03, methanol).

A mixture of (−)-(3aα, 4β, 6aα)-tetrahydro-1,3-dibenzyl-4-(ω-carboxybutyl)-1H-thieno[3,4-d]imidazol-2(3H)-one (0.95 g), phosphoric acid (9.5 ml) and phenol (0.22 ml) was stirred at 150° C. for 3 hours. After cooling, water (100 ml) was added and the mixture was washed with diethyl ether. The aqueous layer was cooled to obtain crystals of D-biotin (285 mg).

mp: 221°−223° C.

Specific rotation: $[\alpha]_D^{30} = +87.2$ (c=1.08, N/10 sodium hydroxide).

What is claimed is:

1. A compound of the formula (I):

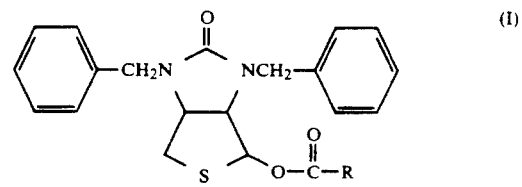

wherein

is an acyl group.

2. A compound according to claim 1, wherein the acyl group is formyl, $C_{1-6}$ alkyl-carbonyl, $C_{6-14}$ aryl-carbonyl or C<sub>7-19</sub> aralkyl-carbonyl which may be substituted with a substituent selected from the group consisting of nitro, halogen, hydroxyl, oxo, carbamoyl, $C_{1-4}$ alkyl, $C_{1-4}$ alkoxy, optionally esterified carboxyl and $C_{1-4}$ alkoxyimino optionally substituted with carboxyl.

3. A compound according to claim 2, wherein the acyl group is $C_{1-6}$ alkyl-carbonyl optionally substituted with carboxyl group.

4. A compound according to claim 1 which is represented by the formula (I'):

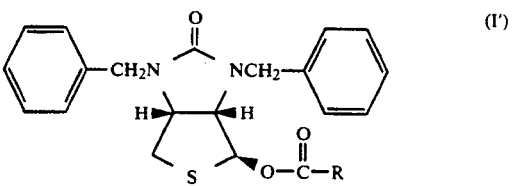

wherein R—CO— group is as defined in claim 1.

5. A compound according to claim 1 which is represented by the formula (I''):

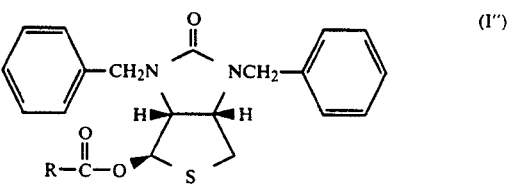

wherein R—CO— group is as defined in claim 1.

6. A compound according to claim 1 that is (±)-(3aα, 4α, 6aα)-tetrahydro-4-acetoxy-1,3-dibenzyl-1H-thieno[3,4-di]imidazol-2(3H)-one.

* * * * *